US012582378B2

(12) United States Patent
Da Cruz et al.

(10) Patent No.: US 12,582,378 B2
(45) Date of Patent: Mar. 24, 2026

(54) METHODS AND SYSTEMS FOR AN INVASIVE DEPLOYABLE DEVICE USING A SHAPE MEMORY MATERIAL TO RECONFIGURE TRANSDUCER ELEMENTS IN RESPONSE TO STIMULI

(71) Applicant: GE Precision Healthcare LLC, Wauwatosa, WI (US)

(72) Inventors: Edouard Da Cruz, Nice (FR); Flavien Daloz, Biot (FR); Kevin M. Durocher, Waterford, NY (US); Reinhold Brüstle, Frankenburg (AT); Bruno Haider, Rehoboth, DE (US); Giandonato Stallone, Nice (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 992 days.

(21) Appl. No.: 17/222,387

(22) Filed: Apr. 5, 2021

(65) Prior Publication Data

US 2022/0313206 A1 Oct. 6, 2022

(51) Int. Cl.
*A61B 8/00* (2006.01)
*A61B 8/12* (2006.01)
(Continued)

(52) U.S. Cl.
CPC ............... *A61B 8/12* (2013.01); *A61B 8/445* (2013.01); *A61B 8/4494* (2013.01); *A61B 18/08* (2013.01);
(Continued)

(58) Field of Classification Search
CPC ......... A61B 8/12; A61B 8/445; A61B 8/4494; A61B 18/08; A61B 2018/00059;
(Continued)

(56) References Cited

U.S. PATENT DOCUMENTS 5,379,772 A * 1/1995 Imran ...................... A61B 8/12
600/463
5,405,337 A * 4/1995 Maynard ........... A61M 25/0158
604/531
(Continued)

FOREIGN PATENT DOCUMENTS

WO WO-2010096174 A1 * 8/2010 ......... A61B 17/1285

OTHER PUBLICATIONS

David Henchi Liang, Byong-Ho Park, Aditya Koolwal, Friedrich Prinz, "A microfabricated intravascular ultrasound scanner for intravascular interventions," Proc. SPIE 5721, MOEMS Display and Imaging Systems III, (Jan. 22, 2005); https://doi.org/10.1117/12.597160 (Year: 2005).*

(Continued)

*Primary Examiner* — Christopher Koharski
*Assistant Examiner* — James F McDonald, III
(74) *Attorney, Agent, or Firm* — Andrus Intellectual Property Law, LLP

(57) ABSTRACT

A deployable invasive device includes a transducer with a plurality of elements with linked by at least one shape memory material, the at least one shape memory material configured to move the plurality of the elements relative to one another between a first configuration and a second configuration in response to the thermal stimulus. The shape memory material comprises at least one active region configured to change shape to facilitate transition between the first configuration and the second configuration. The deployable invasive device further includes at least one integral heating resistor on or within the at least one active region and configured to heat the shape memory material surrounding the integral heating resistor to provide the thermal stimulus.

20 Claims, 17 Drawing Sheets

(51) Int. Cl.
　　*A61B 18/08* 　　　　(2006.01)
　　*A61B 18/00* 　　　　(2006.01)
(52) U.S. Cl.
　　CPC .............. *A61B 2018/00059* (2013.01); *A61B*
　　　　　　　　　　　　　　*2018/0072* (2013.01)
(58) Field of Classification Search
　　CPC ...... A61B 2018/0072; A61B 2017/003; A61B
　　　　　　2017/00867; A61B 8/466; A61B 8/483;
　　　　　　　A61B 8/0883; A61B 8/4488; C22F 1/00
　　See application file for complete search history.

(56) References Cited

U.S. PATENT DOCUMENTS

| | | | | |
|---|---|---|---|---|
| 6,083,170 | A * | 7/2000 | Ben-Haim | A61B 8/06 600/463 |
| 6,551,302 | B1 * | 4/2003 | Rosinko | A61M 25/0147 604/95.04 |
| 7,220,233 | B2 * | 5/2007 | Nita | A61B 17/22012 601/3 |
| 7,500,954 | B2 | 3/2009 | Wilser et al. | |
| 8,206,305 | B2 | 6/2012 | Garbini et al. | |
| 9,655,679 | B2 * | 5/2017 | Desai | A61B 17/3421 |
| 10,405,830 | B2 | 9/2019 | Garbini et al. | |
| 10,522,132 | B2 * | 12/2019 | Hakkens | A61B 8/4281 |
| 2002/0049383 | A1 * | 4/2002 | Swanson | A61B 8/12 600/450 |
| 2007/0066902 | A1 * | 3/2007 | Wilser | B06B 1/0292 600/459 |
| 2007/0067027 | A1 * | 3/2007 | Moaddeb | A61F 2/2448 623/2.37 |
| 2008/0125659 | A1 * | 5/2008 | Wilser | A61B 8/445 600/459 |
| 2008/0125661 | A1 * | 5/2008 | Garbini | G01S 15/8929 600/459 |
| 2008/0146937 | A1 | 6/2008 | Lee et al. | |
| 2012/0108980 | A1 * | 5/2012 | Shilling | G01S 15/894 600/466 |
| 2013/0096426 | A1 * | 4/2013 | Levy | A61B 8/12 600/463 |
| 2013/0296885 | A1 * | 11/2013 | Desai | A61B 17/3417 606/130 |
| 2014/0187961 | A1 * | 7/2014 | Yamakoshi | A61B 1/00089 600/467 |
| 2014/0275986 | A1 * | 9/2014 | Vertikov | A61B 5/062 600/424 |
| 2015/0223781 | A1 * | 8/2015 | Abe | A61B 8/466 600/437 |
| 2017/0157361 | A1 * | 6/2017 | Barrish | A61B 17/00234 |
| 2018/0130457 | A1 * | 5/2018 | Hakkens | A61N 7/022 |
| 2020/0337765 | A1 * | 10/2020 | Smith | A61B 18/1492 |
| 2021/0085935 | A1 * | 3/2021 | Fahey | A61B 17/11 |

OTHER PUBLICATIONS

Tung et al., "Design and Fabrication of Tubular Shape Memory Alloy Actuators for Active Catheters", The First IEEE/RAS-EMBS International Conference on Biomedical Robotics and Biomechatronics, 2006. BioRob 2006., 775, (2006); doi: 10.1109/BIOROB.2006. 1639184 (Year: 2006).*
Komatsubara et al., "Development of the Forward-Looking Active Micro-Catheter Actuated by Ti—Ni Shape Memory Alloy Springs," 2009 IEEE 22nd International Conference on Micro Electro Mechanical Systems, Sorrento, Italy, 2009, pp. 1055-1058 (Year: 2009).*

* cited by examiner

METHODS AND SYSTEMS FOR AN INVASIVE DEPLOYABLE DEVICE USING A SHAPE MEMORY MATERIAL TO RECONFIGURE TRANSDUCER ELEMENTS IN RESPONSE TO STIMULI

BACKGROUND

Embodiments of the subject matter disclosed herein relate to a deployable catheter.

Invasive devices may be used to obtain information about tissues, organs, and other anatomical regions that may be difficult to gather via external scanning or imaging techniques. An invasive device may be a deployable catheter which may be inserted intravenously into a patient's body. In one example, the device may be used for intracardiac echocardiography imaging where the device is introduced into the heart via, for example, the aorta, inferior vena cava, or jugular vein. The device may include an ultrasound probe with an aperture size conforming to dimensions that enables the device to fit through an artery or vein. Thus, a resolution and penetration of the ultrasound probe may be determined by a maximum allowable diameter of the invasive device.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a deployable invasive device includes a transducer with a plurality of elements with linked by at least one shape memory material, the at least one shape memory material configured to move the plurality of the elements relative to one another between a first configuration and a second configuration in response to the thermal stimulus. The shape memory material comprises at least one active region configured to change shape to facilitate transition between the first configuration and the second configuration. The deployable invasive device further includes at least one integral heating resistor on or within the at least one active region and configured to heat the shape memory material surrounding the integral heating resistor to provide the thermal stimulus.

One embodiment of a method of deploying an imaging catheter includes receiving at a control circuit a command to transition a transducer between a first configuration and a second configuration, wherein the transducer comprises a plurality of elements linked by at least one shape memory material configured to move the plurality of elements relative to the one another in response to a thermal stimulus so as to transition between the first configuration and the second configuration. A current through at least one integral heating resistor is controlled to heat at least a portion of the shape memory material to provide the thermal stimulus to transition between the first configuration and the second configuration.

Various other features, objects, and advantages of the invention will be made apparent from the following description taken together with the drawings.

BRIEF DESCRIPTION OF THE DRAWINGS

The present invention will be better understood from reading the following description of non-limiting embodiments, with reference to the attached drawings, wherein below:

FIGS. 1-4 and 6A-9D are drawn approximately to scale although other relative dimensions may be used.

DETAILED DESCRIPTION

Figure 1:
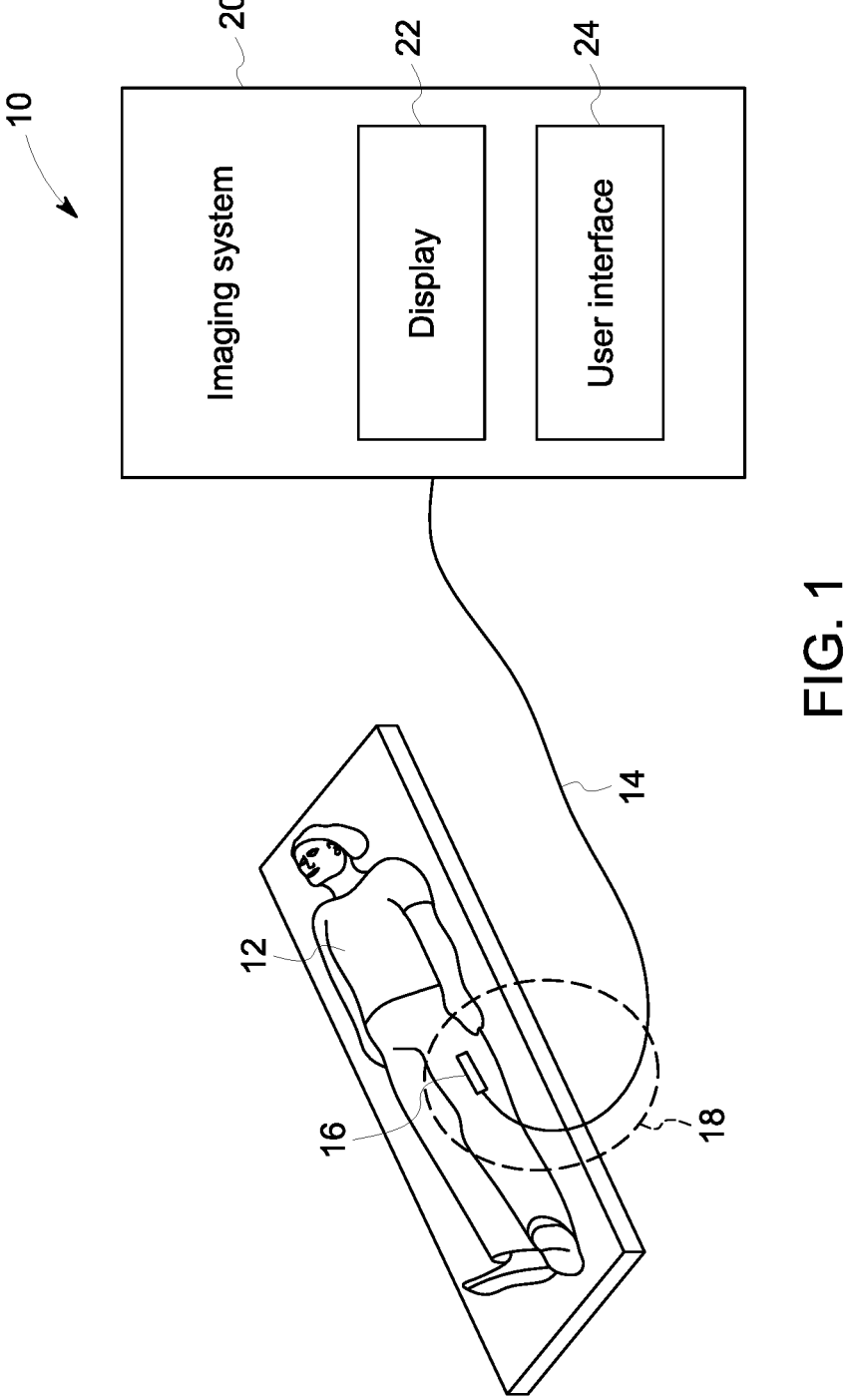
FIG. 1 shows a block diagram of an exemplary imaging system including a deployable catheter.
Figure 2:
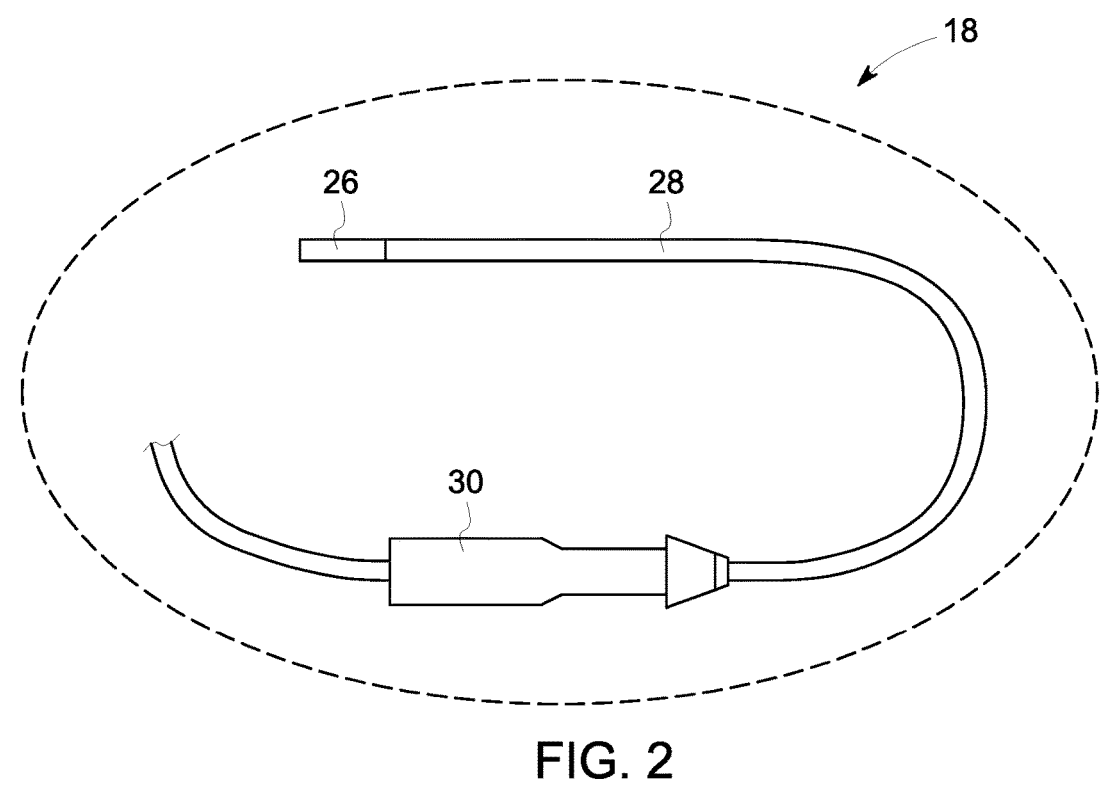
FIG. 2 shows the deployable catheter of FIG. 1 in greater detail, including an exemplary imaging catheter tip and transducer for use in the system illustrated in FIG. 1.

The following description relates to various embodiments of a deployable invasive device. The deployable invasive device may be a deployable catheter in an imaging system and configured to be inserted into a patient to obtain information about internal tissues and organs. An example of an imaging system equipped with a deployable catheter is shown in FIG. 1. A side view of the deployable catheter is depicted in FIG. 2 and inner components of the deployable catheter are illustrated in a first cross-sectional view of the deployable catheter in FIG. 3. A second cross-sectional view of the deployable catheter is shown as a schematic in FIG. 4. Transitioning of a transducer adapted with a shape memory material, which may be included in the deployable catheter, between a first shape and a second shape is shown in FIGS. 5A-5B. FIG. 5A demonstrates the transducer in both a flat planar shape, or configuration, and a folded shape, or configuration. An additional mode of shape transition of the shape memory material is depicted in FIG. 5B, the additional mode including contraction of the shape memory material along at least one dimension. Examples of transducer incorporating the shape memory material in various locations relative to an active area of the transducer and with the transducer in different configurations are shown herein. For example, the shape memory material may be arranged between transducer elements or arrays of transducer elements, as shown in FIGS. 6A-7C, outside of the active area, as shown in FIGS. 8A-9D.

Medical imaging techniques, such as ultrasound imaging, may be used to obtain real-time data about a patient's tissues, organs, blood flow, etc. However, high resolution data for inner cavities of the tissues and organs may be difficult to obtain via external scanning of the patient. In such instances, a deployable catheter outfitted with a probe may be inserted intravenously into the patient and directed to a target site. The deployable catheter may travel through a narrow channel, such as a vein or artery and therefore may have a similar diameter. However, the narrow diameter of the deployable catheter may limit a size of the probe which, in turn, may constrain data quality and acquisition speed provided by the probe. For example, when the probe is an ultrasound probe, a resolution and penetration of the ultrasound probe may be determined by a size of a transducer of the probe. To increase the quality of images generated by the ultrasound probe, a larger transducer then can be enclosed within a housing of the deployable catheter may be demanded. However, the intravenous or other internal cavity or passageways constrain the size of the transducer, and the size will be constrained by the narrowest portion along a path traveled by the catheter from the entry location to the imaging location.

Thus, the inventors have endeavored to develop a deployable invasive device, such as a catheter, having a transducer that can change shape or configuration between a first configuration and a second configuration, where one of the configurations is more compact and/or has a smaller planar area and thus can fit through narrower passageways or cavities within the body. Once the deployable invasive device reaches its imaging location, the transducer can be transitioned to an imaging configuration where the plurality of elements are positioned for imaging, such as positioned adjacent to one another along a flat plane or in an arc. The imaging configuration occupies a larger planar area, or footprint, than the configuration used for insertion and/or movement of the catheter between imaging locations. As will be understood by a person of ordinary skill in the art reviewing the disclosure, the ultrasound transducer may comprise one or more transducer elements, which is the part of the ultrasound transducer that converts between ultrasonic energy and electrical energy, such as comprising piezoelectric or single crystal material or a micro-electromechanical system (MEMS) device. In various embodiments, the plurality of elements may be arranged in one or more transducer arrays.

In certain examples, a shape memory material is incorporated into the deployable catheter and configured to cause or facilitate transition between the first and second configurations. The shape memory material may be a shape memory polymer (SMP) configured to alternate between at least two different shapes. Where the SMP is coupled to or integrated into the transducer, a footprint of a transducer of the deployable catheter, or a planar area occupied by the transducer, may be selectively increased or decreased. The shape-changing behavior of the SMP allows the transducer to have, for example, a first shape with a first set of dimensions enabling the plurality of elements, such as arranged in a plurality of transducer arrays to be readily inserted into the patient's body within the deployable catheter housing. In response to exposure to a stimulus, the SMP may adjust to a second shape with a second set of dimensions that increases a size of the transducer and/or a footprint thereof.

The SMP may be coupled to the transducer via more than one configuration, allowing flexibility in a design of the transducer to accommodate available packaging space and to enhance a performance of the transducer. For example, a positioning of the SMP relative to an active area of the transducer may be varied and/or the SMP may be configured to change shape via more than one mode. In this way, the imaging probe may be in a conformation more favorable for intravenous passage within the patient and subsequently enlarged when deployed in a target anatomical region to obtain high resolution data. By leveraging the SMP to induce shape transitions, a cost of the deployable catheter may be maintained low while allowing for a large range of deformation.

Turning now to FIG. 1, a block diagram of an exemplary system 10 for use in medical imaging is illustrated. It will be appreciated that while described as an ultrasound imaging system herein, the system 10 is a non-limiting example of an imaging system which may utilize a deployable device to obtain medical images. Other examples may include incorporating other types of invasive probes such as endoscopes, laparoscopes, surgical probes, intracavity probes, amongst others. The system 10 may be configured to facilitate acquisition of ultrasound image data from a patient 12 via an imaging catheter 14. For example, the imaging catheter 14 may be configured to acquire ultrasound image data representative of a region of interest in the patient 12 such as the cardiac or pulmonary region. In one example, the imaging catheter 14 may be configured to function as an invasive probe. Reference numeral 16 is representative of a portion of the imaging catheter 14 disposed inside the patient 12, such as inserted into a vein. Reference numeral 18 is indicative of a portion of the imaging catheter 14 depicted in greater detail in FIG. 2.

The system 10 may also include an ultrasound imaging system 20 that is in operative association with the imaging catheter 14 and configured to facilitate acquisition of ultrasound image data. It should be noted that although the exemplary embodiments illustrated hereinafter are described in the context of a medical imaging system, such as an ultrasound imaging system, other imaging systems and applications are also contemplated (e.g., industrial applications, such as nondestructive testing, borescopes, and other applications where ultrasound imaging within confined spaces may be used). Further, the ultrasound imaging system 20 may be configured to display an image representative of a current position of the imaging catheter tip within the patient 12. As illustrated in FIG. 1, the ultrasound imaging system 20 may include a display area 22 and a user interface area 24. In some examples, the display area 22 of the ultrasound imaging system 20 may be configured to display a two- or three-dimensional image generated by the ultrasound imaging system 20 based on the image data acquired via the imaging catheter 14. For example, the display area 22 may be a suitable CRT or LCD display on which ultrasound images may be viewed. The user interface area 24 may include an operator interface device configured to aid the operator in identifying a region of interest to be imaged. The operator interface may include a keyboard, mouse, trackball, joystick, touch screen, or any other suitable interface device.

FIG. 2 illustrates an enlarged view of the portion 18 shown in FIG. 1 of the imaging catheter 14. As depicted in FIG. 2, the imaging catheter 14 may include a tip 26 on a distal end of a flexible shaft 28. The catheter tip 26 may house a transducer and motor assembly. The transducer may include one or more a plurality of transducer elements, such as one or more transducer arrays. The imaging catheter 14 may also include a handle 30 configured to facilitate an operator manipulating the flexible shaft 28.

Figure 3:
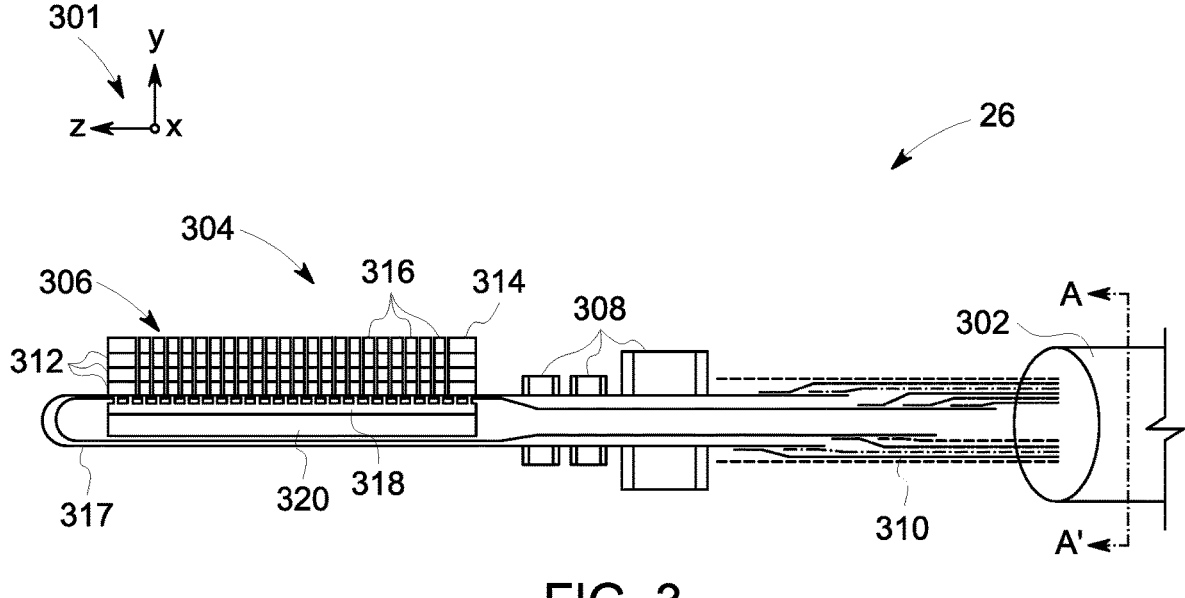
FIG. 3 shows a first cross-sectional view of the exemplary imaging catheter tip which may be included in the deployable catheter of FIG. 2.

An example of the catheter tip 26 of FIG. 2 is shown in FIG. 3. A set of reference axes 301 are provided, indicating a y-axis, an x-axis, and a z-axis. The catheter tip 26 may have a housing 302 surrounding a transducer 304 which may include a plurality of transducer elements arranged in at least one transducer array 306, capacitors 308, and a catheter cable 310. The other components not shown in FIG. 3 may also be enclosed within the housing 302, such as a motor, a motor holder, a thermistor, and an optional lens, for example. Furthermore, in some examples, the catheter tip 26 may include a system for filling the tip with a fluid, such as an acoustic coupling fluid.

As will be understood by a person of ordinary skill in the art reviewing this disclosure, each transducer element may be operated as part of a transducer array (e.g., transducer array 306) or operated as a single transducer element. Likewise, where the term "transducer array" is used in the disclosure, alternative embodiments may instead include a single transducer element in place of an array and any such aspects of the disclosure shall be interpreted as covering both such embodiments. In such an embodiment, each transducer array 306 (or each transducer array 504, 506, 604, 606 discussed in FIGS. 5A and 6A-6B) may instead be a single transducer element. The transducer array 306 has several layers stacked along the y-axis and extending along the x-z plane. One or more layers of the transducer array 306 may be layers of transducer elements 312. In one example, the transducer elements 312 may be piezoelectric elements, where each piezoelectric element may be a block formed of a natural material such as quartz, or a synthetic material, such as lead zirconate titanate, that deforms and vibrates when a voltage is applied by, for example, a transmitter. In some examples, the piezoelectric element may be a single crystal with crystallographic axes, such as lithium niobate and PMN-PT $(Pb(Mg_{1/3}Nb_{2/3})O_3—PbTiO_3)$. The vibration of the piezoelectric element generates an ultrasonic signal formed of ultrasonic waves that are transmitted out of the catheter tip 26. The piezoelectric element may also receive ultrasonic waves, such as ultrasonic waves reflected from a target object, and convert the ultrasonic waves to a voltage. The voltage may be transmitted to a receiver of the imaging system and processed into an image.

In another example, the transducer elements 312 may be micro-electromechanical system (MEMS) devices, including flexible MEMS. Such MEMS-based acoustic transducers may be, for example, CMOS (complimentary metal oxide semiconductor)-based MEMS, micromachined ultrasound transducers (MUTs), including piezoelectric MUTs (pMUTs) and capacitive MUTs (cMUTs).

An acoustic matching layer 314 may be positioned above the transducer elements 312. The acoustic matching layer 314 may be a material positioned between the transducer elements 312 and a target object to be imaged. By arranging the acoustic matching layer 314 in between, the ultrasonic waves may first pass through the acoustic matching layer 314, and emerge from the acoustic matching layer 314 in phase, thereby reducing a likelihood of reflection at the target object. The acoustic matching layer 314 may shorten a pulse length of the ultrasonic signal, thereby increasing an axial resolution of the signal.

The layers formed by the acoustic matching layer 314 and the transducer elements 312 may be diced along at least one of the y-x plane and the y-z plane to form individual acoustic stacks 316. Each of the acoustic stacks 316 may be electrically insulated from adjacent transducers but may all be coupled to common layers positioned below or above the transducer elements, with respect to the y-axis. For example, each acoustic stack 316 may be couples to an electrical circuit, as described below.

An electrical circuit 318 may be layered below, relative to the y-axis, the transducer elements 312. In one example, the electrical circuit may be at least one application specific integrated circuit (ASIC) 318 directly in contact with each of the acoustic stacks 316. Each ASIC 318 may be coupled to one or more flex circuits 317 which may extend continuously between the transducer array 306 and the catheter cable 310. The flex circuits 317 may be electrically coupled to the catheter cable 310 to enable transmission of electrical signals between the transducer array 306 and an imaging system, e.g., the imaging system 20 of FIG. 1. The electrical signals may be tuned by the capacitors 308 during transmission. Various electrical circuit arrangements, including numbers and locations of ASICs 318 are described herein.

An acoustic backing layer 320 may be arranged below the ASIC 318, with respect to the z-axis. In some examples, as shown in FIG. 3, the backing layer 320 may be a continuous layer of material that extends along the x-z plane. The backing layer 320 may be configured to absorb and attenuate backscattered waves from the transducer elements 312. A bandwidth of an acoustic signal generated by the transducer elements 312, as well as the axial resolution, may be increased by the backing layer 320.

As described above, the transducer 304, the capacitors 308, and the catheter cable 310 may be enclosed within the housing 302. Thus a size, e.g., a diameter or width of the components may be determined by an inner diameter of the housing 302. An inner diameter of the housing 302 may be, in turn, determined by an outer diameter and a desirable thickness of the housing 302. The outer diameter of the housing 302 may be constrained by a region of a patient's body through which the imaging catheter is inserted. For example, the imaging catheter may be an intracardiac echocardiography (ICE) catheter used to obtain images of cardiac structures and blood flow inside the patient's heart.

The imaging catheter may be introduced into the heart through the aorta, inferior vena cava, or jugular vein. In some instances, the imaging catheter may be fed through regions with narrower diameters, such as the coronary sinus, the tricuspid valve, and the pulmonary artery. As such, the outer diameter of the imaging catheter may not be greater than 10 Fr or 3.33 mm. The outer diameter and corresponding inner diameter of the imaging catheter housing are shown in FIG. 4 in a cross-section 400 of the housing 302 of the catheter tip 26, taken along line A-A' depicted in FIG. 3.

Figure 4:
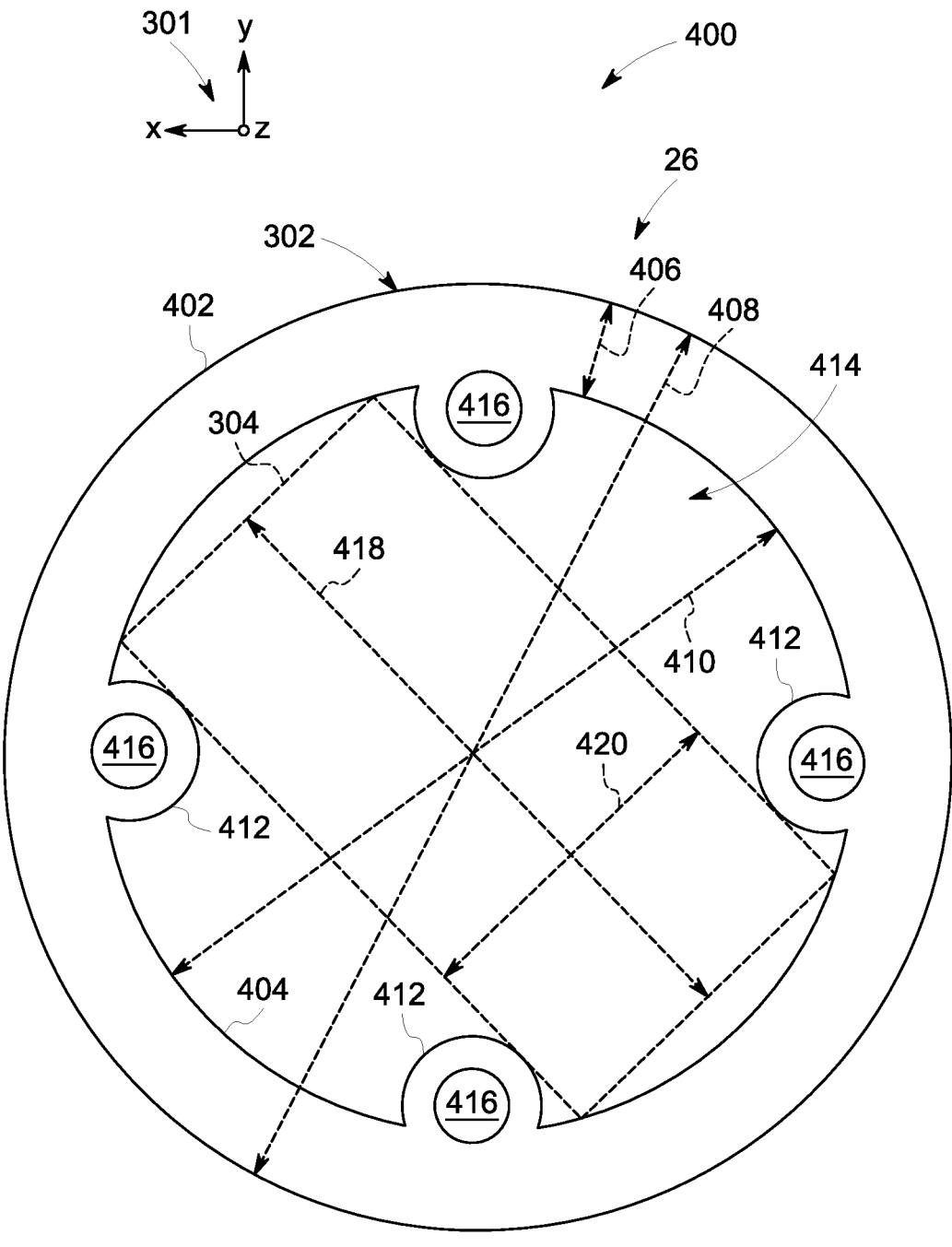
FIG. 4 is a schematic of a second cross-sectional view of the deployable catheter of FIG. 2.
Figure 5A:
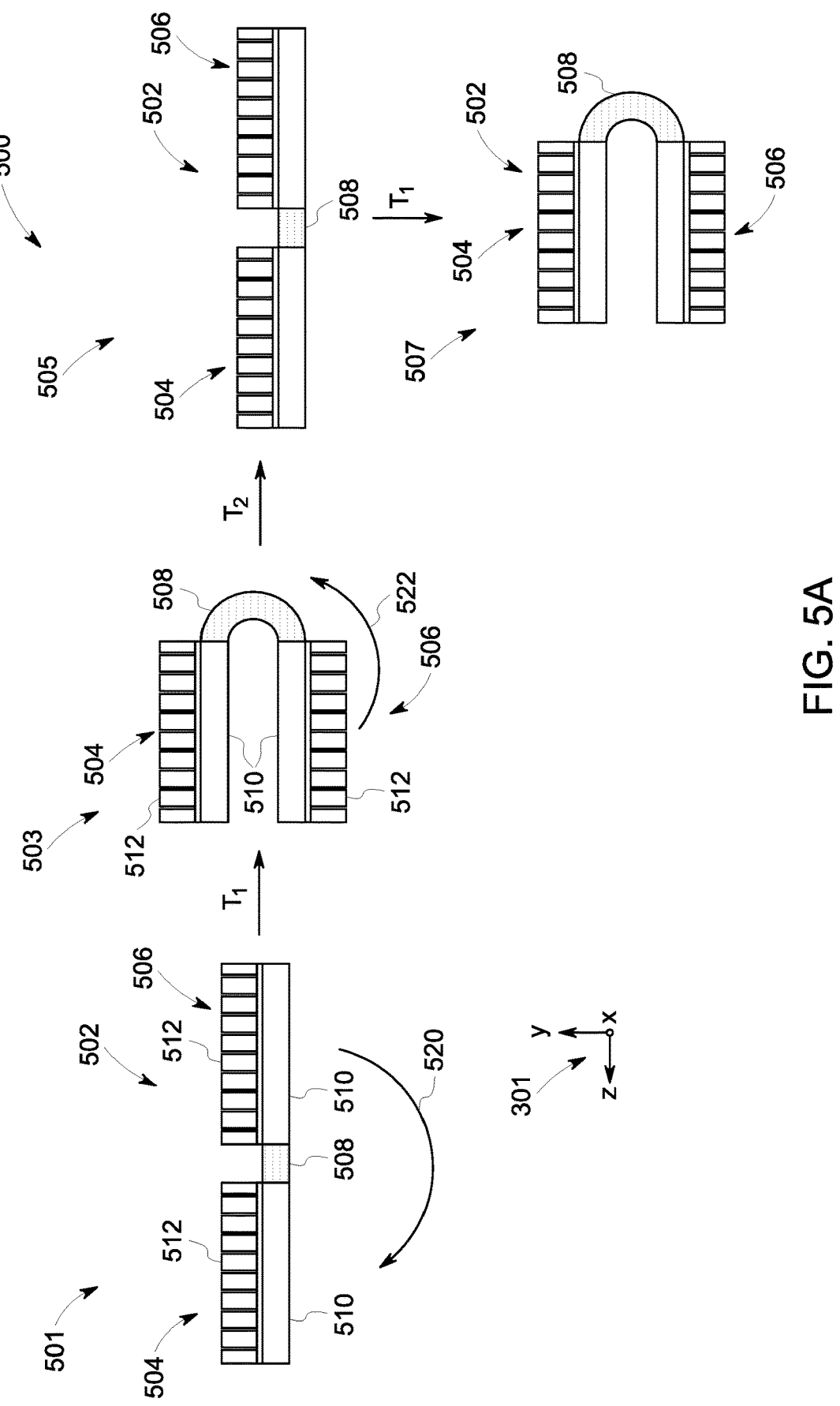
FIGS. 5A and 5B are diagrams showing multi-way shape memory effect of a transducer incorporating a shape memory material.
Figure 5B:
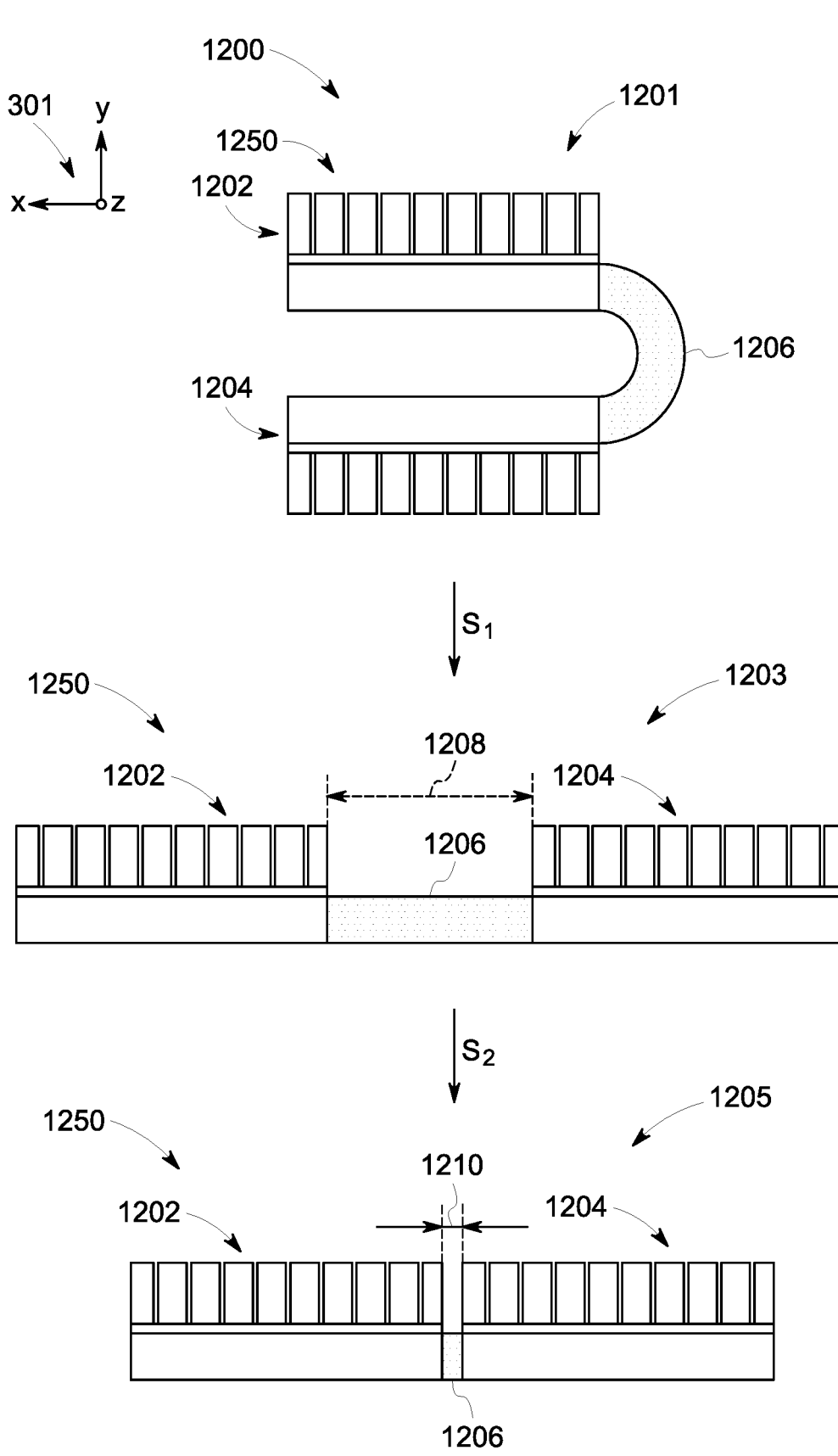

As shown in FIG. 4, an outer surface 402 of the housing 302 of the imaging catheter may be spaced away from an inner surface 404 of the housing 302 by a thickness 406 of the housing 302. The thickness 406 of the housing 302 may be optimized to provide the housing 302 with a target degree of structural stability, e.g. resistance to deformation, balanced with flexibility, e.g., ability to bend when a force is applied. In one example, an outer diameter 408 of the housing 302 may be 3.33 mm, the thickness 406 may be 0.71 mm, and an inner diameter 410 of the housing 302 may be 2.62 mm. In other examples, the outer diameter of the housing may be between 2-5 mm, the thickness may be between 0.24-1 mm, and the inner diameter may be between 1-4 mm. In yet other examples, the imaging catheter may have a variety of dimensions, depending on application. For example, an endoscope may have an outer diameter 10-12 mm. It will be appreciated that the imaging catheter may have various diameters and sizes without departing from the scope of the present disclosure.

The inner surface 404 of the housing 302 may include lobes 412 protruding into an inner volume, or lumen 414 of the housing 302. The lobes 412 may be semi-circular projections, each enclosing an individual lumen 416 for housing a steering wire of the imaging catheter. An arrangement of a transducer 304 of the imaging catheter within the lumen 414 of the housing 302 is indicated by a dashed rectangle. A maximum elevation aperture 418 of the transducer 304 may be determined based on the inner diameter 410 of the housing 302 and a height 420 of the transducer 304 may be configured to fit between the lobes 412 of the housing 302. In one example, the elevation aperture 418 may be a maximum of 2.5 mm and the height 420 may be a maximum of 1 mm.

As described above, dimensions of the transducer 304 may be determined by the inner diameter 410, thickness 406, and outer diameter 408 of the housing 302 which may, in turn, be determined based on insertion of the imaging catheter into specific regions of the patient's anatomy. The constraints imposed on a size of the transducer 304 and diameter 422 of the catheter cable 310, may affect a resolution, penetration, and fabrication of the transducer 304. Each of the resolution, penetration and ease of fabrication may be enhanced by increasing the size of the transducer 304 but the geometry of the transducer 304, and therefore performance, is bound by the dimensions of the catheter housing 302 in order for the deployable catheter to travel intravenously through a patient.

In one example, the transducer may be enlarged upon deployment at a target site by adapting the transducer with a shape memory material. The shape memory material may be a shape memory polymer (SMP) configured to respond mechanically to one or more stimuli. Examples of SMPs include linear block copolymers, such as polyurethanes, polyethylene terephthalate, polyethyleneoxide, and other thermoplastic polymers such as polynorbornene. In one example, the SMP may be a powder mixture of silicone and tungsten in an acrylic resin. The SMP may be stimulated by physical stimuli, such as temperature, moisture, light, magnetic energy, electricity, etc., by chemical stimuli, such as chemicals, pH level, etc., and by biological stimuli, such as presence of glucose and enzymes. When applied to an imaging catheter, the transducer may incorporate the SMP to enable a shape of the transducer to be altered upon exposure to at least one stimulus. The SMP may have physical properties as provided below in Table 1 which may offer more desirable characteristics than other types of shape memory materials, such as shape memory alloys. For example, SMPs may have a higher capacity for elastic deformation, lower cost, lower density, as well as greater biocompatibility and biodegradability. In particular, the lower cost of SMPs may be desirable for application in disposable deployable catheters.

TABLE 1

| Physical Properties of Shape Memory Polymers | |
| --- | --- |
| Property | Range |
| Density (g/cm$^3$) | 0.2-3 |
| Extent of deformation | Up to 800% |
| Required stress for deformation (MPa) | 1-3 |
| Stress generated upon recovery (MPa) | 1-3 |
| Transition temperature (° C.) | −10 to 100 |
| Recovery speed | 1 s to 1 HR |
| Processing condition | <200° C.; low pressure |
| Cost | <$10/lb |

In one example, the SMP may have two-way shape memory so that the SMP may adjust between two shapes without demanding reprogramming or application of an external force. For example, the SMP may convert to a temporary shape in response to a first stimulus and revert to a permanent shape in response to a second stimulus. The first and second stimuli may be of a same or different type, e.g., the first stimulus may be a high temperature and the second stimulus may be a low temperature or the first stimulus may be a humidity level and the second stimulus may be thermal, such as a threshold temperature. The two-way shape memory behavior is neither mechanically nor structurally constrained, thereby allowing the SMP to switch between the temporary shape and permanent shape without applying the external force.

As an example, conversion of a transducer 502 between a first shape and a second shape in response to a thermal stimulus is shown in a first diagram 500 in FIG. 5A. The transducer 502 includes a first transducer array 504 and a second transducer array 506 where the second transducer array 506 is aligned with the first transducer array 504 along the z-axis and spaced away from the first transducer array 504. In other words, the transducer 502 has an overall planar shape with the first and second transducer arrays 504, 506 co-planar with one another along a common plane, e.g., the x-z plane. A first step 501 of the first diagram 500, depicts coupling of an SMP 508 to a backing layer 510 of each of the first and second transducer arrays 504, 506. The SMP 508, configured as a two-way memory SMP, is arranged between the transducer arrays along the z-axis and may be fixedly attached to edges of the backing layers 510 and arranged co-planar with the backing layers 510. For example, the backing layers 510 and the SMP 508 arranged therebetween may form a continuous, planar unit. Transducer elements 512 are laminated onto the backing layer 510 of the first and second transducer arrays 504, 506.

In some examples, the SMP 508 may form a continuous layer entirely across the transducer 502. The SMP 508 may, for example, be an acoustic layer of the transducer 502, such as a matching layer or a backing layer. By incorporating the SMP 508 as an acoustic layer, an assembly and number of components of the transducer may be simplified without adversely affecting a reduction in size of the transducer footprint. Implementing the SMP as an acoustic layer of the transducer is discussed further below, with reference to FIGS. 10-11.

The transducer 502 is exposed to a first temperature, $T_1$, and, at a second step 503, the SMP 508 changes shape in response to $T_1$. The SMP 508 may bend into a semi-circular shape, pivoting the second transducer array 506 substantially through 180 degrees along a first rotational direction, e.g., clockwise, as indicated by arrow 520. Bending, as referred to herein, may be any transitioning of a planar structure to a non-planar conformation. As such, various deformations of the structure from a configuration that is aligned with a plane may be considered bending.

When the SMP 508 bends, the transducer 502 may therefore also bend. While the SMP may bend through a range of angles, bending of the SMP so that two regions of the transducer 502 become stacked over one another and substantially parallel with one another is referred to as folding herein. The SMP, in some examples, may not bend to an extent that the transducer is folded. However, folding of the transducer may provide a most compact conformation of the transducer to enable passage of the deployable catheter through intravenous passages.

As a result of the folding of the transducer 502, the second transducer array 506 is positioned under the first transducer array 504, with respect to the y-axis, in a folded shape. An overall planar surface area of the transducer elements 512, including the transducer elements 512 of both the first and second transducer arrays 504, 506, is reduced at the second step 503 compared to the first step 501 when viewing the transducer 502 along the y-axis.

The transducer 502 is exposed to a second temperature, $T_2$, and, in response, the SMP 508 reverts to the planar geometry of the first step 501 at a third step 505 of the first diagram 500. The second transducer array 506 is pivoted substantially through 180 degrees along a second rotational direction, opposite of the first rotational direction, e.g., counterclockwise. The second temperature $T_2$ may be a higher or lower temperature than $T_1$. Subjecting the transducer 502 to $T_1$ again compels the SMP 508 to bend, folding the transducer 502 so that the second transducer array 506 is pivoted 180 degrees at a fourth step 507.

As described above, the transducer 502 may be enclosed within a housing at a tip of a deployable catheter, such as the housing 302 of FIGS. 3 and 4. To accommodate unfolding of the transducer 502 to the planar geometry, the housing may be formed of a flexible, elastic material that stretches and deforms as the transducer 502 changes shape. For example, the deployable catheter may be a balloon catheter and the housing at the catheter tip may be an inflatable balloon. The balloon may be formed from a material such as polyester, polyurethane, silicone, etc. and may be inflated by filling the balloon with a fluid or a gas. Prior to adjustment of the transducer 502 to the planar geometry, the balloon may be inflated to allow the transducer 502 to transition without impediment. Upon adjustment of the transducer 502 to the folded conformation, the balloon may be deflated by venting or draining the gas or fluid.

The steps shown in the first diagram 500 may be repeated many times. For example, prior to insertion of an imaging catheter adapted with the transducer 502 into a patient, the transducer may be initially exposed to one or more stimuli to fold and decrease the size of the transducer 502. The folded transducer 502, may fit within a housing of an imaging catheter and inserted intravenously into the patient. When the transducer 502 reaches a target site within the patient, the transducer 502 may be unfolded and/or otherwise enlarged by subjecting the array to $T_2$. Images may be obtained while the transducer 502 is unfolded and increased in size. For example, unfolding the transducer 502 may increase an elevation aperture of the transducer 502.

When scanning is complete, the transducer 502 may be exposed again to the stimulus or to a different stimulus to cause the transducer 502 to fold and decrease in size. The imaging catheter may then be withdrawn from the site and removed from the patient or deployed to another site for imaging within the patient. Thus, the shape and size of the transducer 502 may be adjusted between the planar and folded configurations numerous times during an imaging session.

A second diagram 1200 is shown in FIG. 5B which illustrates a second embodiment of a transducer comprising SMP and configured to change shapes between an insertion shape that occupies a smaller footprint and an imaging shape where the transducer arrays are positioned for imaging. It will be appreciated that the configurations of the transducers 502, 1202 shown in FIGS. 5A and 5B are non-limiting examples of shapes that the transducer may transition between. Other examples may include the transducer 502 being in a non-planar geometry at the first step 501, such as slightly bent or curved shape, becoming more bent or curved at the second step 503, and alternating between the less bent/curved and more bent/curved shapes upon exposure to one or more stimuli. In addition, the transducer 502 may fold so that the first and second transducer arrays 504, 506, are not parallel with one another. In yet other examples, the first and second transducer arrays 504, 506 may be different sizes.

Furthermore, when the SMP 508 forms an entire layer across the transducer 502, rather than forming a section between the backing layers 510 of the first and second transducer arrays 504, 506, the SMP 508 may be adapted to change shape only in an area between the transducer arrays. In one example the SMP 508 may be able to change shape via more than one type of transition. For example, the SMP 508 may bend upon exposure to one type of stimulus and shrink upon exposure to another type of stimulus. In another example, the SMP 508 may include more than one type of shape memory material. As an example, the SMP 508 may be formed of a first type of material configured to bend and a second type of material configured to shrink. Other variations in shape transitions, combination of materials, and positioning of the SMP 508 within the transducers have been contemplated.

While temperature changes are described as a stimulus for inducing changes in the SMP shape for the first diagram 500 of FIG. 5A, it will be appreciated that the first diagram 500 is a non-limiting example of how deformation of the SMP may be triggered. Other types of stimuli, such as humidity, pH, UV light, etc. may be used to induce mechanical changes in the SMP. More than one type of stimulus may be applied to the SMP to achieve similar or different shape modification. Furthermore, deformation of the SMP may include other manners of shape change other than bending. For example, the SMP may curl into a jellyroll configuration or shrink along at least one dimension. Details of the mechanical deformation are described further below.

Referring now to FIG. 5B, a transducer 1202 is configured to change shape via more than one transition path, which may be caused by exposure of the SMP 1206 to more than one stimulus type or intensity. For example, the SMP may fold, in response to a first stimulus, and contract along at least one dimension, in response to a second stimulus. The SMP may have a large deformation capability of, for example, up to 800%. By using an SMP adapted to contract along at least one dimension in response to a stimulus, the distance between transducers may be decreased. As shown in the second diagram 1200 of FIG. 5B, a transducer 1250 has a first transducer array 1202 and a second transducer array 1204 spaced apart from the first transducer array 1202 by a SMP 1206. The transducer 1250 is depicted in a first, folded configuration 1201, where an active area of the transducer 1250 is reduced and the footprint is reduced relative to a second, unfolded configuration 1203.

Upon exposure to a first stimulus, $S_1$, the SMP 1206 transitions to the second configuration 1203. The first stimulus $S_1$ may be any of the stimuli described herein. An active area of the transducer 1250, e.g., a total surface area of the transducer 1250 facing a same direction along the y-axis, is doubled relative to the first configuration 1201. The first transducer array 1202 is spaced away from the second transducer array 1204 by the SMP 1206 which has a first width 1208 in the second configuration 1203, the width defined along the x-axis which may also be an elevation direction of the transducer 1250. Thus, a planar area, or footprint, occupied by the transducer is increased between the first configuration 1201 and the second configuration 1203.

The SMP 1206 may be exposed to a second stimulus $S_2$, different from the first stimulus $S_1$, which may compel the SMP 1206 to shrink along the x-axis. In one example, the first stimulus $S_1$ may be temperature and the second stimulus $S_2$ may be humidity. In other examples, the first and second stimuli $S_1$, $S_2$ may be any combination of various chemical, physical, and biological stimuli. A contraction of the SMP 1206 along the elevation direction transitions the transducer 1250 into a third, contracted configuration 1205. In the third configuration 1205, the SMP 1206 has a second width 1210 which is smaller than the first width 1208. The distance between the first and second transducer arrays 1202, 1204 is thus reduced. Thus, a planar area, or footprint, occupied by the transducer is decreased between the second configuration 1203 and the third configuration 1205.

The transducer 1250 may transition from the third configuration 1205 to the second configuration 1203 and from the second configuration 1203 to the first configuration 1201 by exposing the SMP 1206 to more than one stimulus. The SMP 1206 may be similarly applied to transducers with more than two transducer arrays, such as the described below with respect to FIGS. 9A-9D.

To return the transducer 1250 to the first configuration 1201, the transducer 1250 may be exposed to a variation of the second stimulus $S_2$ to expand the SMP 1206 along the x-axis. For example, if the second stimulus $S_2$ is pH, the SMP 1206 may be subjected to a first, lower pH to induce contraction and a second, higher pH to facilitate expansion. The transducer 1250 may then be exposed to a variation of the first stimulus $S_1$ to induce bending of the SMP 1206 to fold the transducer 1250. For example, if the first stimulus $S_1$ is humidity, the transducer 1250 may be exposed to a lower humidity to compel bending of the SMP 1206 and higher humidity to trigger straightening of the SMP 1206.

The contracting and expanding of the SMP 1206 allows the spacing between transducer arrays to be adjusted based on response of the SMP 1206 to stimuli. When the SMP 1206 is configured as sections arranged between the transducer arrays and coupled to inner edges of the transducer arrays, as shown in FIGS. 6A-7B, the entire section of the SMP may contract and expand. Furthermore, the SMP 1206 may, in some examples, be configured to contract and expand along the azimuth direction in addition to or instead of the elevation direction. By constraining the region of contraction and expansion, undesirable separation of the SMP from transducer components coupled to the SMP may be mitigated.

It will be appreciated that the examples of shape transitions described above, e.g., bending and contracting, are non-limiting examples. Various other modes of shape change have been contemplated for use in a deployable catheter. For example, in addition to bending and contracting, the SMP may curl, twist, and/or expand. The SMP may be configured to change shape via more than more mode depending on an applied stimulus and a desired level of complexity.

In this way, a transducer for a deployable catheter may readily pass intravenously through a patient and provide images with enhanced field of view, resolution, penetration, and image update rate. Transducer arrays of the transducer may be linked to one another by a SMP and/or mounted on an SMP and the transducer may transition between at least a first, folded shape and a second, unfolded shape as a result exposure of the SMP to stimuli. In an alternative embodiment, the SMP may be positioned between and link a plurality of transducer elements together and be configured to move the plurality of transducer elements with respect to one another. An active area of the transducer may be selectively increased, enhancing a performance of the transducer. The SMP may be incorporated in the transducer via more than one configuration. For example, the SMP may be attached to edges of the transducer arrays and extend between the transducer arrays. Alternatively, the SMP may form a continuous, common acoustic layer of the transducer arrays and bend at regions between the transducer arrays. To decrease a distance between the transducer arrays during data acquisition, the SMP may be configured to contract along at least one dimension. Furthermore, when packaging space is available along an azimuth aperture of the transducer, the SMP may be located outside of the active area of the transducer, also resulting in a decrease in the distance between the transducer arrays. As such, a data quality and speed of data acquisition of the transducer may be increased at low cost while allowing the transducer to be adjusted to a conformation favorable for intravenous passage of the deployable catheter.

Figure 6A:
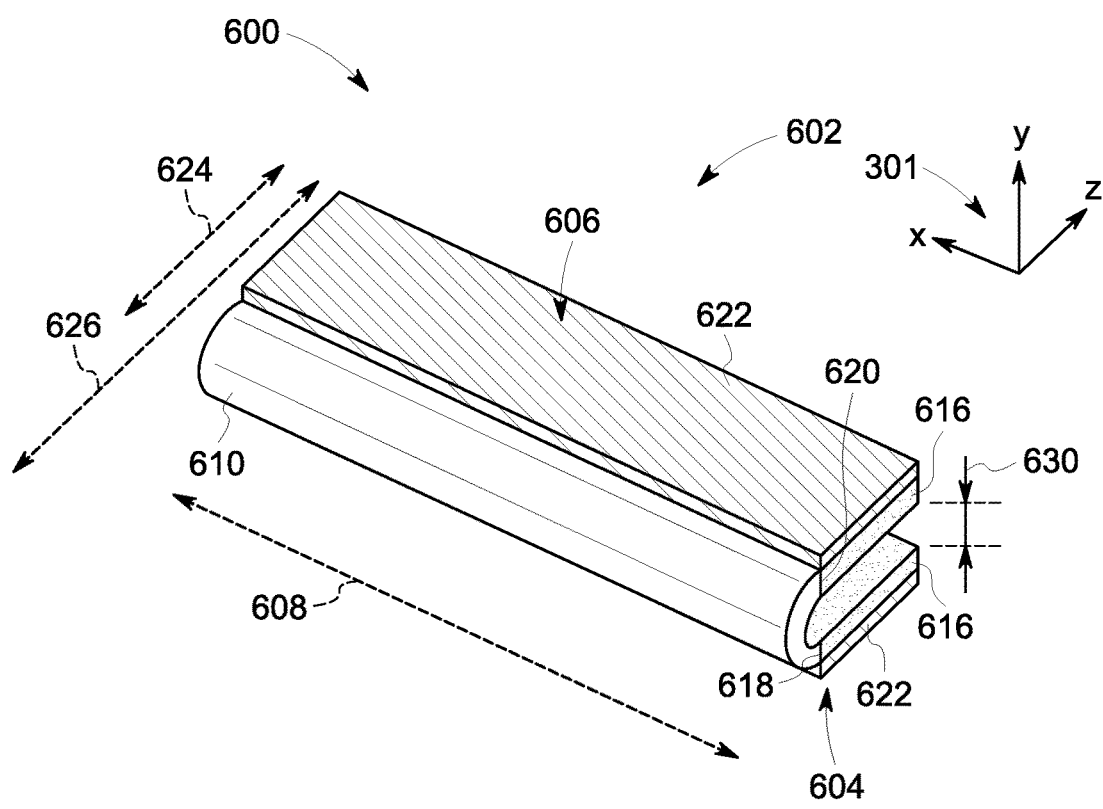
FIG. 6A shows a first example of a transducer adapted with a shape memory material in a folded configuration.
Figure 6B:
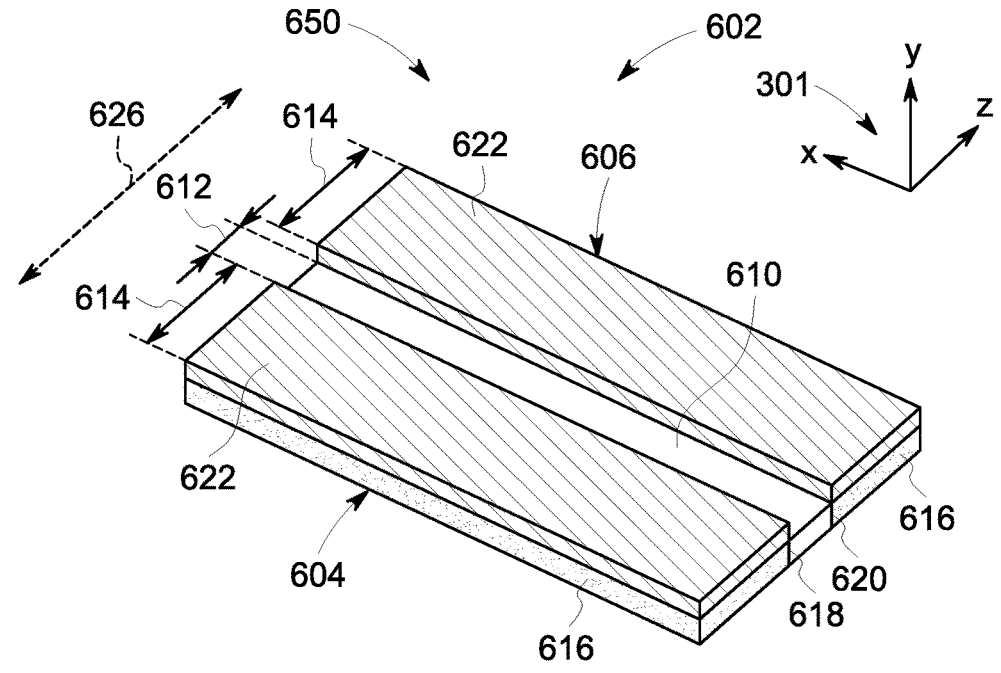
FIG. 6B shows the first example of the transducer of FIG. 6A in an unfolded configuration.

In some examples, as shown in FIGS. 5A and 5B, a transducer of a deployable catheter may include two sections, or two transducer arrays. Each transducer array may include one or more acoustic stacks, including, as described above with reference to FIG. 2, a matching layer and/or a backing layer. An ASIC may be coupled to each transducer array. Alternatively, one ASIC may be coupled to two or more transducer arrays. An exemplary transducer 602 incorporating a SMP to enable modification of an active area of the transducer 602 is shown in FIGS. 6A and 6B. The transducer 602 is shown in a first, folded configuration 600 in FIG. 6A and in a second, unfolded configuration 650 in FIG. 6B.

The transducer 602 has a first transducer array 604 and a second transducer array 606. The first and second transducer arrays 604, 606 have similar dimensions and are each rectangular and longitudinally aligned with the x-axis, e.g., a length 608 of each transducer array is parallel with the x-axis. A SMP 610 is arranged between the transducer arrays, along the z-axis. In other words, the first transducer array 604 is spaced away from the second transducer array 606 by a width 612 of the SMP 610, as shown in FIG. 6B. The width 612 of the SMP 610 may be less than a width 614 of each of the first and second transducer arrays 604, 606 while a length of the SMP 610, defined along the x-axis, may be similar to the length 608 of the transducer arrays.

The SMP 610 may be connected to inner edges of a backing layer 616 of each of the first and second transducer arrays 604, 606. For example, the SMP 610 may be directly in contact with and adhered to a longitudinal inner edge 618 of the backing layer 616 of the first transducer array 604, e.g., an edge of the backing layer 616 facing the second transducer array 606 and aligned with the x-axis, and to a longitudinal inner edge 620 of the backing layer 616 of the second transducer array 606, e.g., an edge of the backing layer 616 facing the first transducer array 604 and aligned with the x-axis. A thickness of the SMP 610 may be similar to a thickness of the backing layer 616 of each of the first and second transducer arrays 604, 606, the thicknesses defined along the y-axis. A matching layer 622 is stacked above the backing layer 616 of each of the transducer arrays. An element, e.g., a piezoelectric element, may be arranged between the matching layer 622 and the backing layer 616 (not shown in FIGS. 6A and 6B).

When in the first configuration 600 as shown in FIG. 6A, the SMP 610 is curved into a semi-circular shape. The second transducer array 606 is stacked directly over, with respect to the y-axis, and spaced away from the first transducer array 604, so that both transducers are maintained co-planar with the x-z plane. The transducer 602 is folded in FIG. 6A so that each matching layer 622 of the transducer arrays face away outwards and away from one another and the backing layers 616 of the transducer arrays face one another. The backing layers 616 may be spaced away from one another by a distance 630 similar to a diameter of the semi-circle formed by the SMP 610. However, in other examples, the transducer 602 may be folded in an opposite direction so that the backing layers 616 of the transducer arrays face one another and the matching layers 622 face away from one another.

As the transducer 602 transitions between the first and second configurations 600, 650, at least one of the transducer arrays are pivoted, for example, 180 degrees relative to the other transducer array. For example, when adjusting from the first configuration 600 to the second configuration 650, the first transducer array 604 may be pivoted through a first rotational direction to become co-planar with the second transducer array 606. Alternatively, the second transducer array 606 may be pivoted 180 degrees through a second rotational direction, opposite of the first rotational direction. The first transducer array 604 may be pivoted through the second rotational direction or the second transducer array 606 may be pivoted through the first rotational direction to return the transducer 602 to the first configuration 600. In another example, both transducer arrays may be pivoted through 90 degrees to achieve transitioning between the first and second configurations 600, 650. It will be appreciated that description of the pivoting of the transducer arrays through 180 degrees is for illustrative purposes and other examples may include the transducer arrays pivoting more or less than 180 degrees.

In the first configuration 600, a width 624 of the transducer 602 is reduced relative to a width 626 of the transducer 602 in the second configuration 650. An active area of the transducer 602 may be equal to a surface area of one of the first or second transducer arrays 604, 606. In the second configuration 650, with the first and second transducer arrays 604, 606 co-planar with one another and side-by-side, the active area of the transducer 602 is doubled relative to the first configuration 600. As such, an elevation aperture of the transducer 602 is at least doubled when unfolded into the second configuration 650, thereby increasing a resolution and penetration of the transducer 602.

In another example, a transducer of an imaging probe may include more than two sections or transducer arrays. A second example of a transducer 702 is shown in a first, folded configuration 700 in FIGS. 7A and 7C, and a second, unfolded configuration 750 in FIG. 7B. The transducer 702 includes a first transducer array 704, a second transducer array 706, and a third transducer array 708. All three transducer arrays may have similar dimensions and geometries and may be connected by a first SMP 710 and a second SMP 712.

Figure 7A:
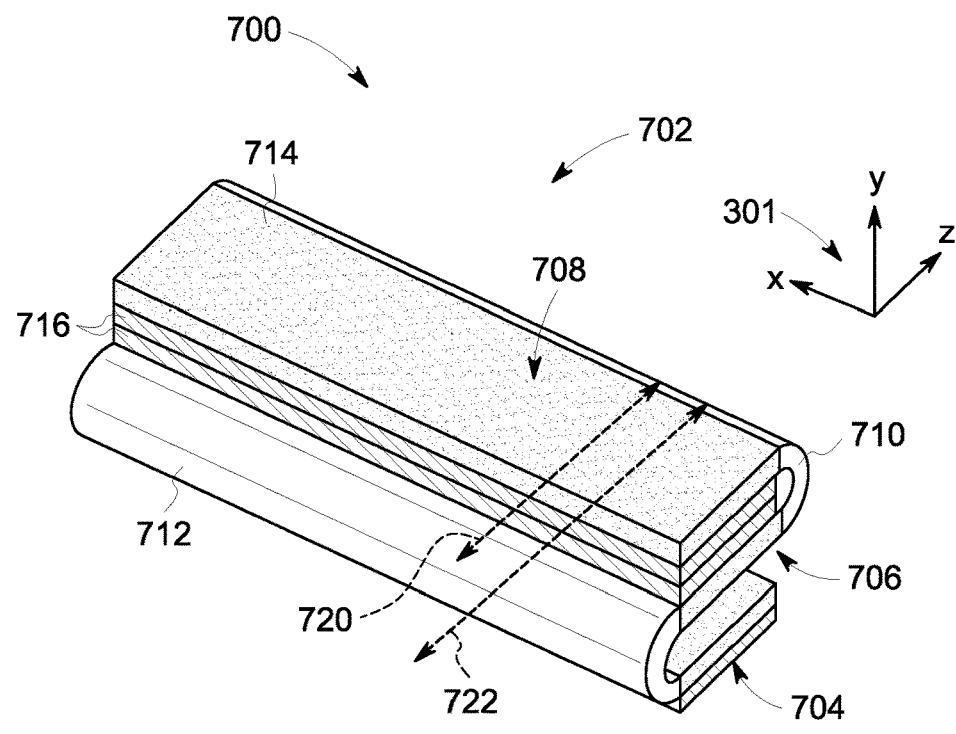
FIG. 7A shows a second example of a transducer adapted with a shape memory material in a folded configuration.
Figure 7B:
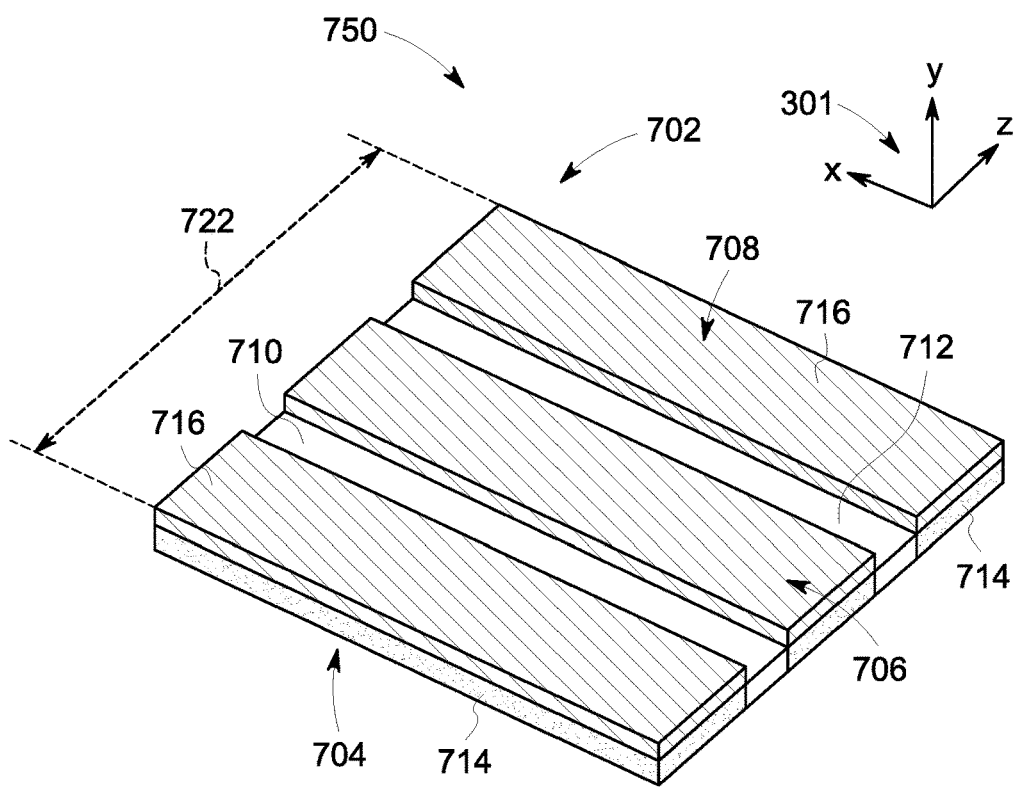
FIG. 7B shows the second example of the transducer of FIG. 7A in an unfolded configuration.

For example, the transducer arrays may be spaced away from one another but co-planar and aligned along the x-axis and z-axis in the second configuration 750 of FIG. 7B. The first transducer array 704 is spaced away from the second transducer array 706 by the first SMP 710 and the second transducer array 706 is spaced away from the third transducer array 708 by the second SMP 712. As described above for the first example of the transducer 602 of FIGS. 6A-6B, the SMPs may be directly connected to longitudinal inner edges of the transducer arrays along a backing layer 714 of each transducer array. The SMPs may be co-planar and have a similar thickness to the backing layer 714 of the transducer arrays. A matching layer 716 of each of the transducer arrays is positioned above the backing layer 714 and aligned with each backing layer 714 along the y-axis. As such, the matching layer 716 protrudes above the first and second SMPs 710, 712 with respect to the y-axis. An element may be arranged between the matching layer 716 and the backing layer 714 (not shown in FIGS. 7A and 7B).

Figure 7C:
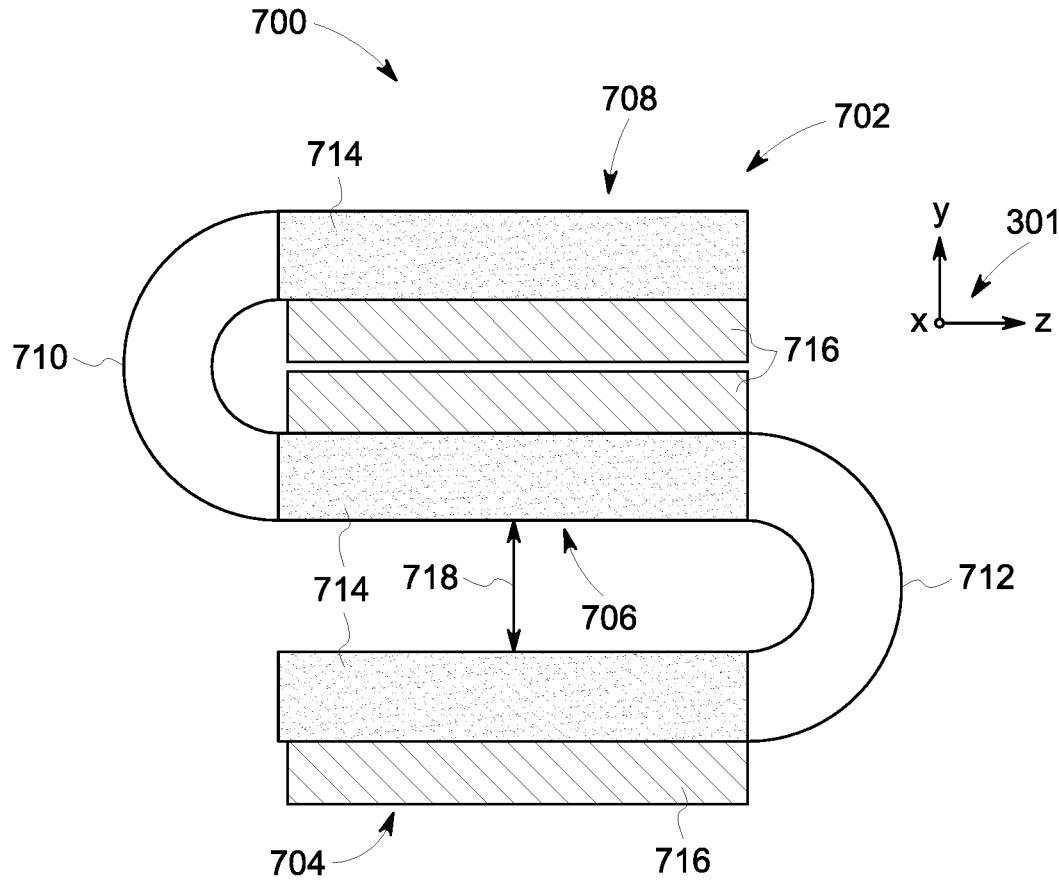
FIG. 7C is a cross-sectional view of the second example of the transducer of FIG. 7A in the folded configuration.

In the first configuration 700 of FIG. 7A, the transducer 702 is folded into an S-shaped geometry when viewed along the x-axis, as shown in FIG. 7C. In the S-shaped geometry, the first SMP 710 is bent into a semi-circle, forming a right half of a circle. The first transducer array 704 may be pivoted through a first rotational direction relative to the second transducer array 706 so that the second transducer array 706 is stacked over and aligned with the first transducer array 704 with respect to the y-axis. While the backing layer 714 of the second transducer array 706 and the backing layer 714 of the first transducer array 704 face each other with no other component of the transducer 702 positioned therebetween, the backing layer 714 of the transducer arrays are spaced apart by a distance 718 similar to a diameter of the semi-circle formed by the first SMP 710.

The second SMP 712 is bent in an opposite direction from the first SMP 710, into a semi-circle forming a left half of a circle. The bending of the second SMP 712 causes the third transducer array 708 to be stacked over the second transducer array 706 along the y-axis. The third transducer array 708 is pivoted through a second rotational direction, opposite of the first rotation direction, so that the third transducer array 708 is aligned with both the first and second transducer arrays 704, 706, along the y-axis and the matching layer 716 of the third transducer array 708 faces the matching layer 716 of the second transducer array 706. The matching layers 716 of the second and third transducer arrays 706, 708 are separated by a gap that is smaller than the distance 718 between the backing layers 714 of the first and second transducer arrays 704, 706.

As the transducer 702 transitions between the first and second configurations 700, 750, at least the first and third transducer arrays 704, 708, may be pivoted through 180 degrees in opposite rotation directions, relative to the second transducer array 706. For example, when adjusting from the first configuration 700 to the second configuration 750, the first transducer array 704 may be pivoted through a first rotational direction to become co-planar with the second transducer array 606. The third transducer array 708 may be pivoted through a second rotational direction, opposite of the first rotational direction to also become co-planar with the second transducer array 606. To return the transducer 702 to the first configuration 700 from the second configuration 750, the first transducer array 704 may be pivoted 180 degrees through the second rotational direction and the second transducer array 706 may be pivoted 180 degrees through the first rotational direction. Alternatively, on other examples, the transducer arrays may be pivoted opposite of the transitioning described above. It will be appreciated that description of the pivoting of the transducer arrays through 180 degrees is for illustrative purposes and other examples may include the transducer arrays pivoting through more or less than 180 degrees.

A width 720, as shown in FIG. 7A, of the transducer 702 in the first configuration 700 may be narrower than a width 722 of the transducer 702 in the second configuration 750. An active area of the transducer 702, determined by a total transducer array surface area along the x-z plane, may be increased threefold when the transducer 702 is adjusted from the first configuration 700 to the second configuration 750. Thus, when a transducer is formed of three transducer arrays (a 3-section transducer, hereafter), and the unfolded 3-section transducer, e.g., the second configuration 750 of FIG. 7B, is equal in size to an unfolded transducer with two transducer arrays (a 2-section transducer, hereafter), e.g., the second configuration 650 of FIG. 6B, the transducer arrays of the 3-section transducer may be narrower in width than the transducer arrays of the 2-section transducer. When folded, the 3-section transducer may have a smaller footprint than the 2-section transducer and may thereby be inserted through narrower channels.

Alternatively, the transducer arrays of the 3-section and 2-section transducers may be similar in size. When folded, both the transducers may have a similar footprint. However, when deployed and unfolded in a target scanning site, the 3-section transducer may have a larger active area, allowing the 3-section transducer to have greater resolution and penetration than the 2-section transducer. Furthermore, the first and second examples of the transducer shown in FIGS. 6A-7C are non-limiting examples. Other examples may include transducers with more than three sections, or transducers and transducer arrays with different geometries and dimensions from those shown.

The folding of a transducer compelled by an SMP, as illustrated in FIGS. 5-7C, may be leveraged to allow the transducer to be implemented in a deployable catheter, such as the imaging catheter 14 of FIG. 1, without inhibiting passage of the deployable catheter through narrow arteries and veins. Thus, a transducer may be selected based on a desired footprint of the folded and/or unfolded transducer. For example, when the 3-section and 2-section transducers have a similar footprint in the folded configuration, the 3-section transducer may be used when a target imaging site with more volume than when the 2-section transducer is used.

Positioning a SMP between each transducer array of a transducer, as shown in FIGS. 6A-7C, allows the transducer to be varied in size along an elevation direction of the transducer. However, if a distance between the transducer arrays of the transducer is too large, an image quality generated by the transducer may be degraded. For example, in order to maintain the enhanced performance of a transducer provided by increasing an active area of the transducer, the distance between each transducer array of the transducer may be cumulatively no more than a threshold percentage, such as 5%, of a total active elevation aperture of the transducer. Thus, minimizing the distance between the transducer arrays during data acquisition at the transducer is desirable. However, folding of the transducer along an azimuth aperture, as shown in FIGS. 5A-5B, 6A and 7A may be a shape transition offering a lowest degree of complexity and easily initiated. To facilitate efficient packaging of the transducer by folding, a total spacing of the distances between the transducer arrays greater than the threshold percentage of the total active elevation aperture may be demanded.

Figures 8A, 8B:
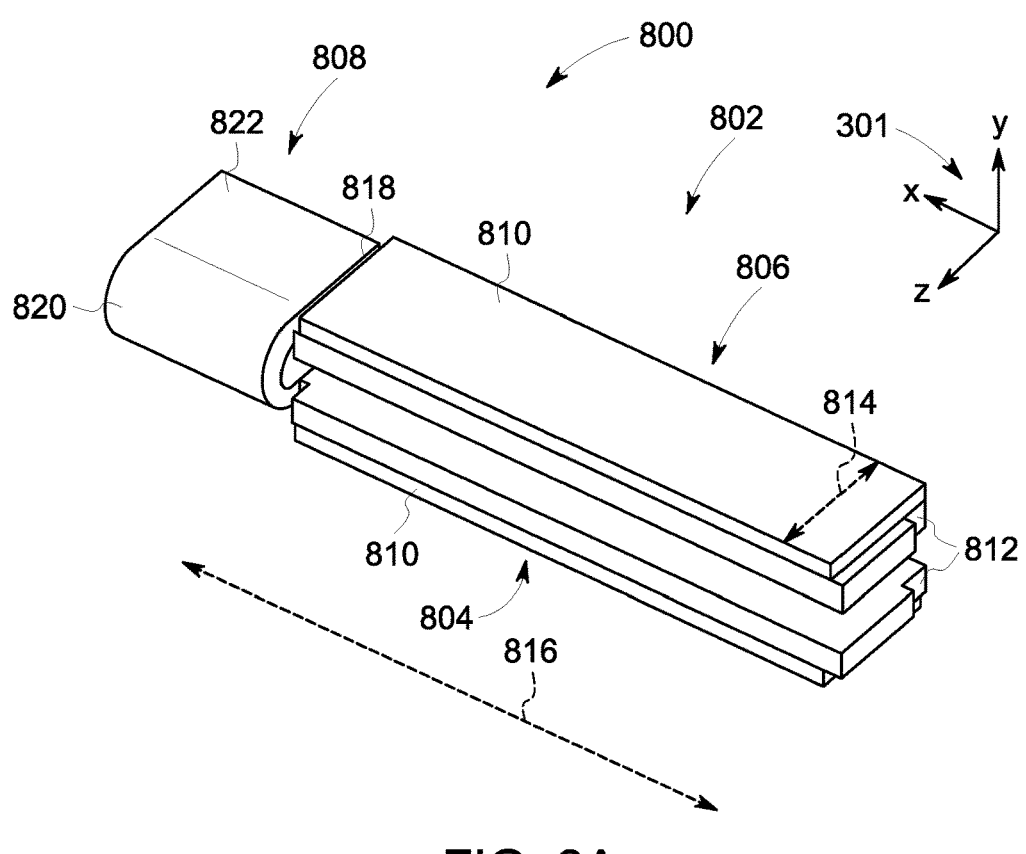
FIG. 8A shows a perspective view of a third example of a transducer adapted with a shape memory material in a folded configuration.
FIG. 8B shows an end view of the third example of the transducer of FIG. 8A.

FIG. 5B shows one example of systems and configurations for decreasing the distance between transducer arrays. Another way that the distance between transducer arrays when the transducer is unfolded may be by positioning the SMP outside of the active area of the transducer. Such an arrangement is referred to as an external arrangement of the SMP hereafter. Relocating the SMP outside of the active area, along the azimuth aperture of the transducer may allow bending of the transducer to be displaced away from the transducer arrays, alleviating a demand for a minimum distance between the transducer arrays to enable sufficient bending of the SMP. A first example of a transducer 802 equipped with an externally arranged SMP is shown in FIGS. 8A-8D. The transducer 802 is depicted in FIG. 8A in a folded configuration from a perspective view 800 and in FIG. 8B from an end view 830. The transducer 802 is further illustrated in FIG. 8C in a perspective view 850 showing the transducer 802 in a transitional configuration and in FIG. 8D in a perspective view 870 of the transducer 802 in an unfolded configuration.

As shown in FIG. 8A, the transducer 802 includes a first transducer array 804, a second transducer array 806, and a SMP 808 positioned at one end of the first and second transducer arrays 804, 806 along the x-axis, which may also be an azimuth direction of the transducer 802. The transducer arrays may be aligned longitudinally with the azimuth direction and parallel with one another. The first and second transducer arrays 804, 806 are not directly coupled to one another, e.g., the transducer arrays may come into contact with one another during shape transitions but are not attached to one another at any point. Each of the transducer arrays has a matching layer 810 and a backing layer 812. The first and second transducer arrays 804, 806 may have similar widths 814 and similar lengths 816, as shown in FIG. 8A, and may both be longitudinally aligned with the x-axis and parallel with one another.

Figure 8C:
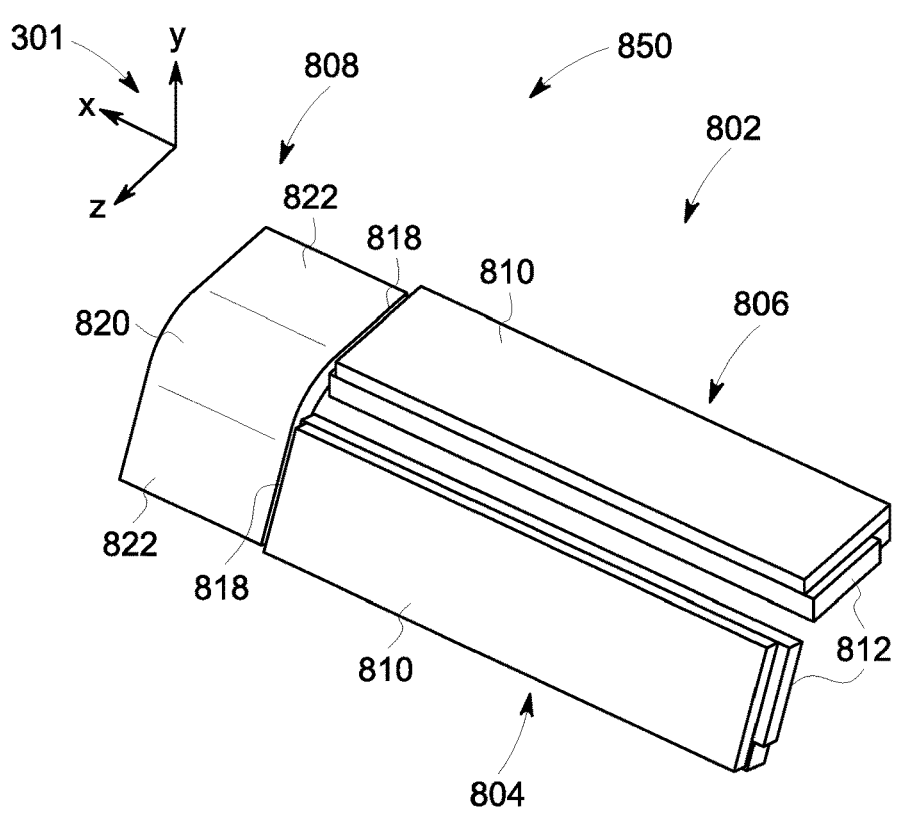
FIG. 8C shows a perspective view of the third example of the transducer of FIG. 8A in a transitional configuration.
Figure 8D:
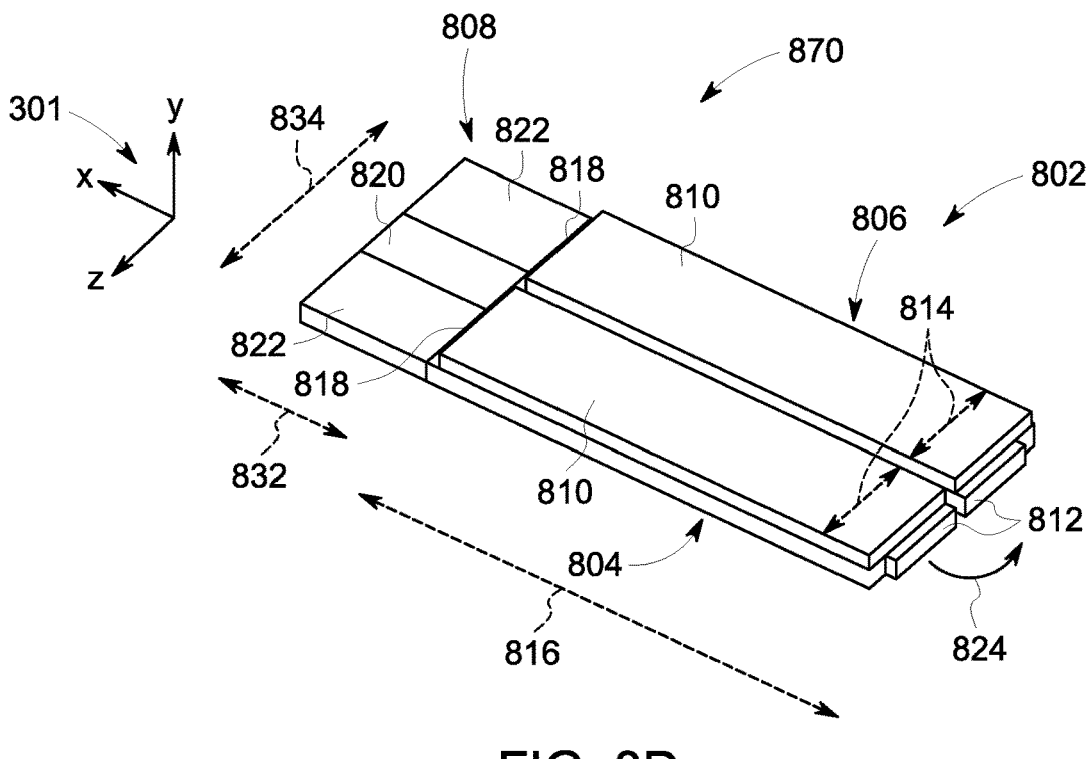
FIG. 8D shows a perspective view of the third example of the transducer of FIG. 8A in an unfolded configuration.

The SMP 808 is coupled to a first edge 818 of the backing layer 812 of each of the transducer arrays, as shown in FIGS. 8A, 8C and 8D, by an adhesive, for example. In other examples, however, when the SMP has attenuating properties, such as when the SMP is configured as a matching layer, the SMP may be a part of the transducer arrays, e.g., integrated into the transducer arrays. The first edge 818 is parallel with the z-axis and extends along the width 814 of each transducer array. A thickness of the SMP 808 may be less than a thickness of each of the transducer arrays, the thicknesses defined along the y-axis, so that the matching layers 810 protrude higher along the y-axis than the SMP 808, as shown in FIG. 8D. An active region 820 of the SMP 808 is not attached to the transducer arrays and is configured to bend as shown in FIGS. 8A, 8B, and 8C. The active region 820 is positioned between planar regions 822 of the SMP 808 which do not bend due to coupling of the planar regions 822 to the first edge 818 of the backing layer 812 of each of the transducer arrays.

In the folded configuration depicted in FIGS. 8A and 8B, the SMP 808 is bent so that the planar regions 822 are stacked over one another along the y-axis and the active region 820 forms a semi-circle. The bending of the SMP 808 causes the first transducer array 804 to fold under the second transducer array 806 to become stacked under the second transducer array 806 along the y-axis. For example, the first transducer array 804 may be pivoted, as indicated by arrow 824 shown in FIG. 8D, through 180 degrees in a first rotational direction, e.g., counterclockwise, relative to the unfolded configuration. In some examples, the first transducer array 804 may be pivoted greater than 180 degrees, such as 190 or 210 degrees, or any angle less than 180 degrees. It will be appreciated that while pivoting of the first transducer array 804 is described, in other examples, the second transducer array 806 may be pivoted instead.

When adjusted to the folded configuration, the backing layers 812 of the first transducer array 804 and the second transducer array 806 may face one another, separated by distance equal to a diameter 826 of the semicircle formed by the active region 820 of the SMP 808, as shown in FIG. 8B. In the folded configuration, an active area of the transducer 802 may be a total surface area of the transducer facing one direction. As such, the active area may be equal to an area of one of the transducer arrays.

In the folded configuration, the transducer 802 may have a sufficiently small footprint to fit within an outer housing of a deployable catheter for intravenous passage. Upon reaching a target imaging site, the transducer 802 may be expanded to the unfolded configuration shown in FIG. 8D. As the transducer 802 unfolds, a straightening of the SMP 808 causes the first transducer array 804 to be rotated in a second rotational direction, opposite of the direction indicated by arrow 824, e.g., clockwise, passing through the transitional configuration shown in FIG. 8C. The first and second transducer arrays 804, 806 are separated by a gap extending longitudinally between the transducer arrays until the transducer 802 is in the unfolded configuration of FIG. 8D.

As shown in FIG. 8D, the transducer 802 is planar, e.g., co-planar with the x-z plane, including both the first and second transducer arrays 804, 806 and the SMP 808. The active region 820, or central region, of the SMP 808 is co-planar with the planar regions 822, together forming a rectangular extension of the transducer 802 along the x-axis. A width 834 of the SMP 808 may be similar to a sum of the widths 814 of the transducer arrays and a length 832 of the SMP 808 is less than the length 816 of the transducer arrays.

The first and second transducer arrays 804, 806 may be positioned very close to one another in the unfolded configuration, e.g., the first and second transducer arrays 804, 806 are contiguous, without any other transducer components arranged in a region of space in between the transducer arrays. The region between the transducer arrays may be defined or bound by inner edges of the transducer arrays and by edges of the transducer arrays perpendicular to the azimuth direction. The transducer arrays may be separated by a small gap or, in some examples, inner edges of the backing layer 812 of each transducer array may be in contact when the transducer 802 is unfolded. The active area of the transducer 802 may be doubled relative to the folded configuration and a distance between the transducer arrays may be smaller than when the SMP is positioned between the transducer arrays. For example, the total distance between the transducer arrays may be less than 5% of the elevation aperture of the transducer 802.

Figures 9A, 9B:
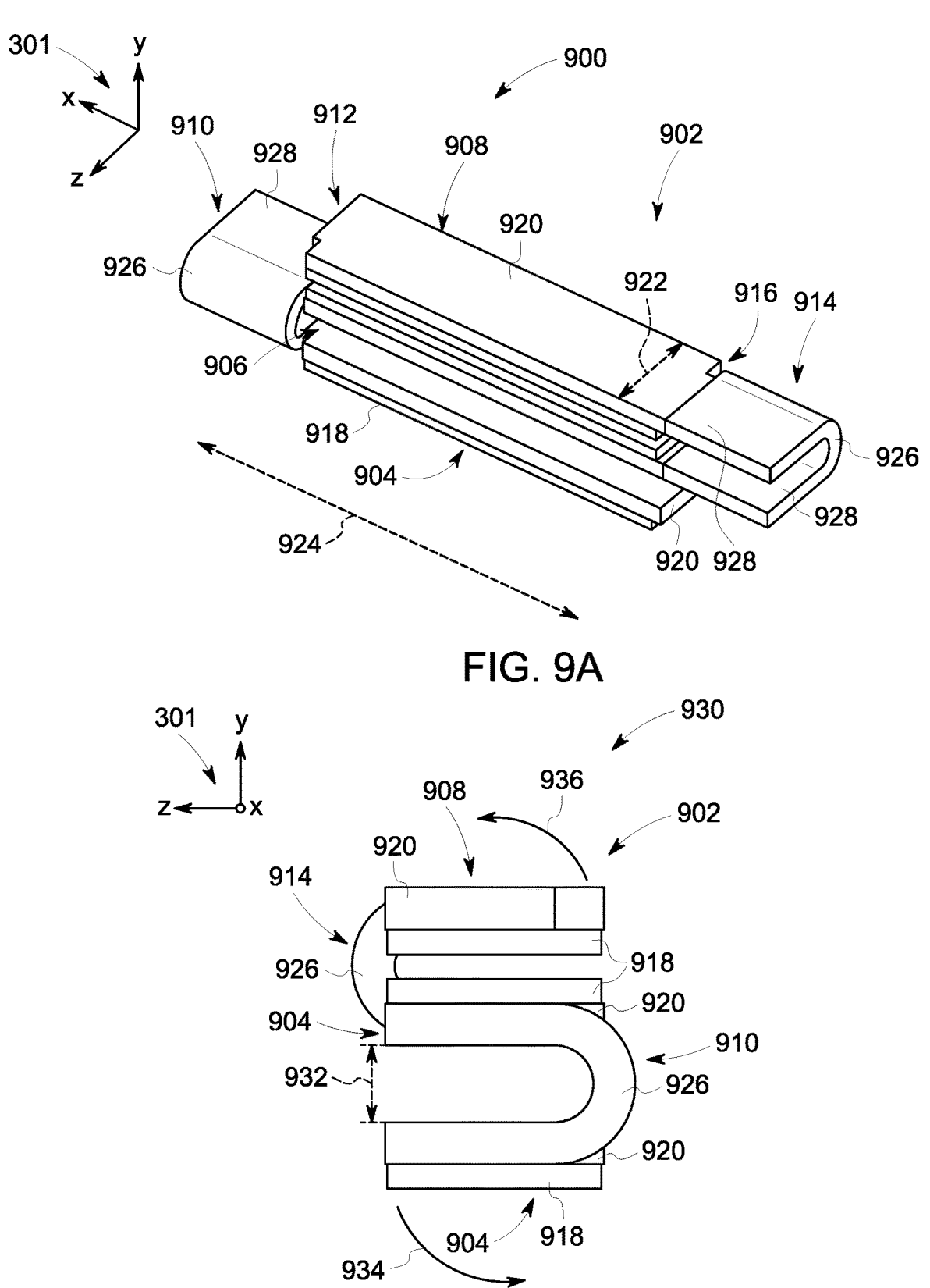
FIG. 9A shows a perspective view of a fourth example of a transducer adapted with a shape memory material in a folded configuration.
FIG. 9B shows an end view of the fourth example of the transducer of FIG. 9A.
Figure 9C:
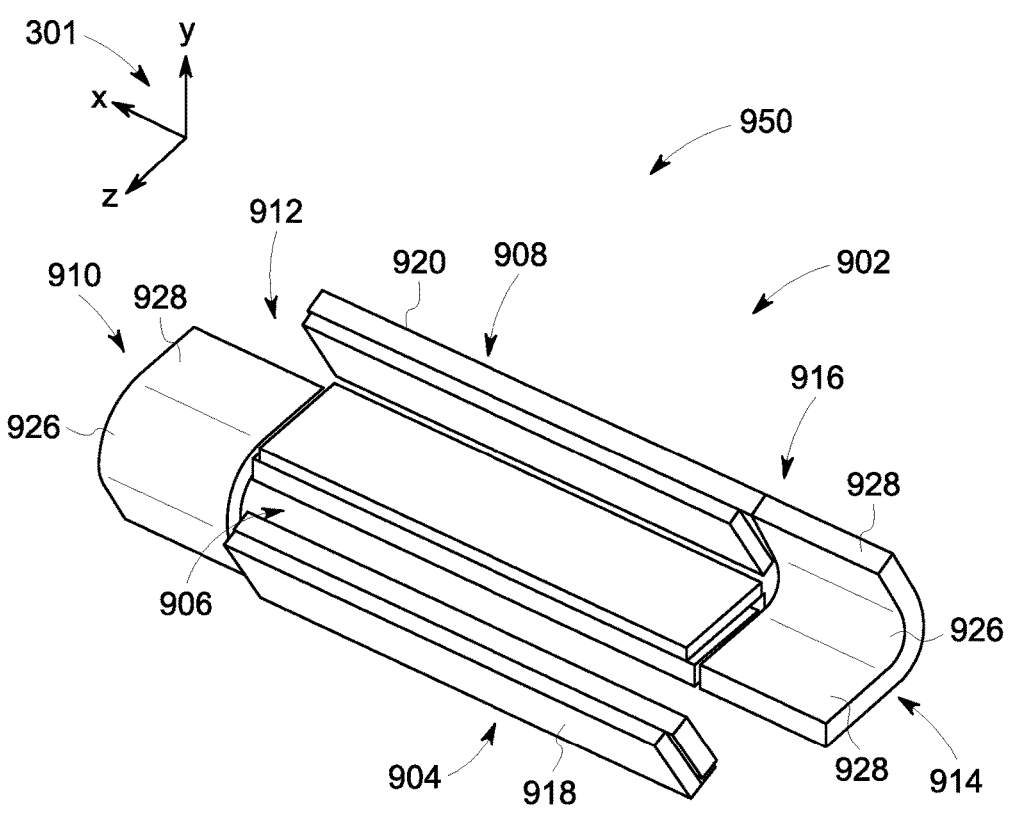
FIG. 9C shows a perspective view of the fourth example of the transducer of FIG. 9A in a transitional configuration.

An active area of a transducer may be more than doubled by adapting the transducer with more than two transducer arrays. As shown in FIGS. 9A-9D, a second example of a transducer 902, equipped with two externally arranged SMPs, may include a first transducer array 904, a second transducer array 906, and a third transducer array 908. The transducer arrays may be longitudinally aligned with the azimuth direction (e.g., the x-axis) and parallel with one another. The transducer 902 is depicted in FIG. 9A in a folded configuration from a perspective view 900 and in FIG. 9B from an end view 930. The transducer 902 is further illustrated in FIG. 9C in a perspective view 950 showing the transducer 902 in a transitional configuration and in FIG. 9D in a perspective view 970 of the transducer 902 in an unfolded configuration.

The transducer 902 may include a first SMP 910 positioned at first end 912 of the transducer 902 and a second SMP 914 positioned at a second end 916 of the transducer 902. The first and second SMPs 910, 914 may each be attached to two of the transducer arrays and may be formed of a same or different material. More specifically, the first SMP 910 is coupled to the first transducer array 904 and the second transducer array 906 at the first end 912 and the second SMP 914 is coupled to the second transducer array 906 and the third transducer array 908 at the second end 916. Each of the transducer arrays has a matching layer 918 and a backing layer 920 and may each have similar widths 922 and similar lengths 924, as shown in FIG. 9A. The transducer arrays may each be longitudinally aligned with the x-axis. A thickness of each of the first and second SMPs 910, 914 may be similar to one another and less than a thickness of each of the transducer arrays, the thicknesses defined along the y-axis, so that the matching layers 918 protrude higher along the y-axis than the SMPs in the unfolded configuration of FIG. 9D.

The second transducer array 906 is positioned between the first transducer array 904 and the third transducer array 908 and the transducer arrays are not directly coupled to one another. Instead, the transducer arrays are linked by the first and second SMPs 910, 914 and transitioning of the transducer 902 between the folded and unfolded configurations are guided by the SMPs. Each of the SMPs includes a central region, or active region 926 configured to flex, and planar regions 928 arranged on opposite sides of the active region 926, or central region. The planar regions 928 are in edge-sharing contact with edges of the backing layers 920 of the transducer arrays and fixedly coupled to the edges of the backing layers 920.

When adjusted to the folded configuration shown in FIGS. 9A and 9B, the first SMP 910 may bend so that the first transducer array 904 is pivoted through, for example, 180 degrees in a first rotational direction, relative to the unfolded configuration of FIG. 9D, to become stacked below the second transducer array 906 along the y-axis. The second SMP 914 may bend in an opposite direction from the first SMP 910 so that the third transducer array 908 is pivoted through, for example, 180 degrees in a second rotational direction, opposite of the first rotational direction, to become stacked above the second transducer array 906 along the y-axis. As described above, other examples may include rotation of the first and third transducer arrays 904, 908 through more or less than 180 degrees. Furthermore, in other examples, the transducer 902 may be folded in an opposite configuration, e.g., the first transducer array 904 over the second transducer array 906 and the third transducer array 908 under the second transducer array 906. In the folded configuration, the stacked transducer arrays are aligned along the y-axis but spaced apart from one another, as shown in FIG. 9B.

The end view 930 of FIG. 9B shows an S-shaped geometry of the transducer. The backing layers 920 of the first and second transducer arrays 904, 906 face one another in the folded configuration while the matching layers 918 of the second and third transducer arrays 906, 908 face one another. The first and second transducer arrays 904, 906 are spaced apart by a distance similar to a diameter 932 of the semi-circle formed by the first SMP 910. The second and third transducer arrays 906, 908 are spaced apart by a distance that is smaller than a diameter of the semi-circle formed by the second SMP 914. The transducer arrays are therefore not in contact with one another when the transducer 902 is in the folded configuration.

When the transducer transitions from the folded configuration to the unfolded configuration, the first SMP 910 may straighten, causing the first transducer array 904 to be pivoted through the second rotational direction as indicated by arrow 934 in FIG. 9B. The second SMP 914 may also straighten, swinging the third transducer array 908 along the first rotational direction, as indicated by arrow 936 in FIG. 9B. The transducer 902 may pass through the transitional configuration shown in FIG. 9C with the transducer arrays still spaced apart and not in contact with one another.

Figure 9D:
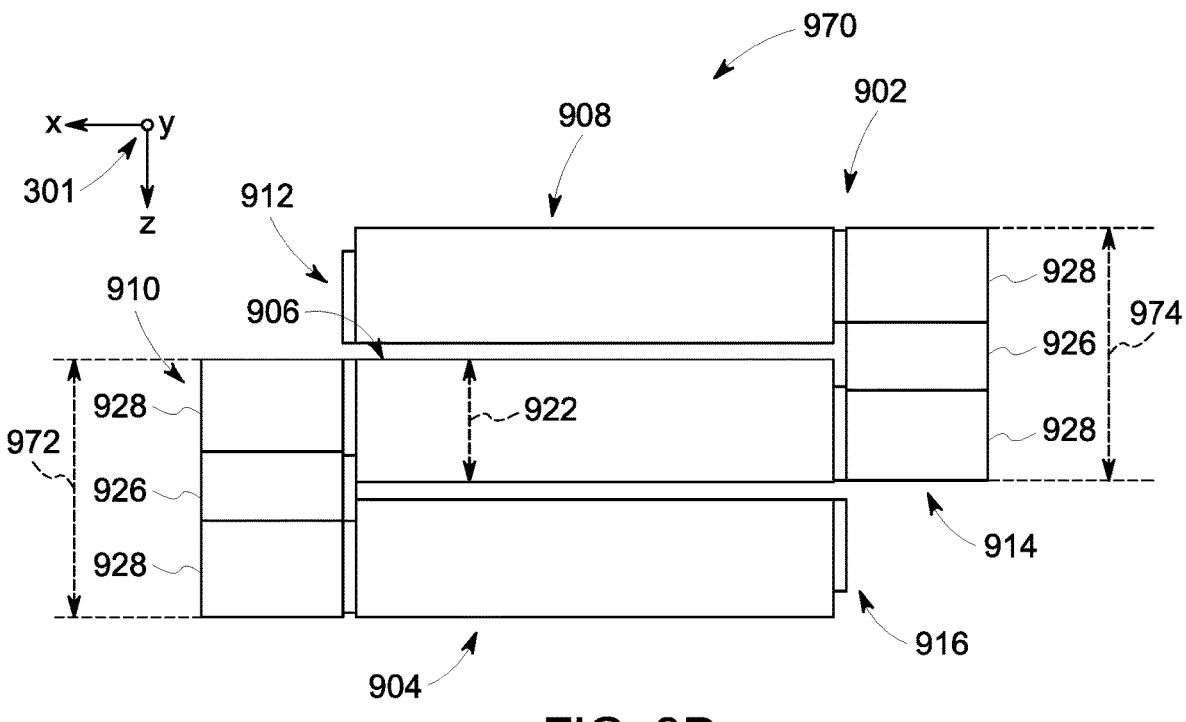
FIG. 9D shows a perspective view of the fourth example of the transducer of FIG. 9A in an unfolded configuration.

The first and second SMPs 910, 914 become aligned with the x-z plane, e.g., flat, in the unfolded configuration shown in FIG. 9D. The SMPs form rectangular extensions along the x-axis at opposing sides of the transducer 902 and may be offset from one another along the x-axis. For example, the first SMP 910 has a width 972 similar or slightly greater than the combined widths 922 of the first and second transducer arrays 904, 906 and is positioned at the first end 912 of the transducer 902. The second SMP 914 has a width 974 similar or slightly greater than the combined widths 922 of the second and third transducer arrays 906, 908 and is positioned at the second end 916 of the transducer 902. The second SMP 914 is positioned higher than the first SMP 910 with respect to the z-axis.

In the unfolded configuration, the transducer arrays are aligned along the x, y, and z-axes and co-planar with one another along a common plane. The transducer arrays are depicted spaced away from one another by a small gap which is less than a distancing of the transducer arrays when the SMPs are instead arranged between the transducer arrays. In some examples, the transducer arrays may be in edge-sharing contact in the unfolded configuration, e.g., inner edges of the transducer arrays are in contact with one another. As described above for the transducer 802 shown in FIGS. 8A-8D, the first, second, and third transducer arrays 904, 906, and 908 are arranged contiguously when the transducer 902 is unfolded, without any other transducer components arranged in regions of space in between the transducer arrays. The regions between the transducer areas may be defined or bound by inner edges of the transducer arrays and by edges of the transducer arrays perpendicular to the azimuth direction.

An active area of the transducer 902 may be tripled when the transducer 902 is unfolded relative to when the transducer is folded when the transducer arrays are similar in size. By placing the SMPs outside of the active area, the transducer arrays are positioned closer together and a total distance between the transducer arrays may thereby be less than 5% of an elevation aperture of the transducer. The external arrangement of the SMP may allow the distance between the transducer arrays to be reduced without introducing additional complexity to a shape transition of the SMP or to a manufacturing process of the transducer. The SMP may be arranged external to the active area of the transducer when packaging space along the azimuth direction of the transducer is not constrained.

As shown in FIGS. 5-9D, a SMP may be attached to a backing layer of a transducer, e.g., to individual backing layers of each transducer array of the transducer. Alternatively, the SMP may be similarly coupled to a matching layer of each transducer array, in some examples. The material of the SMP may be selected to be physically compatible with a material of the backing layer to reduce a likelihood of separation between the SMP and the matching layer or backing layer during transitioning of the SMP between shapes. A fabrication and material selection may be simplified, however, by incorporating the SMP as an acoustic layer of the transducer. As such, the SMP may form either the backing layer or the matching of the transducer, as shown in FIGS. 10-11.

Figure 10:
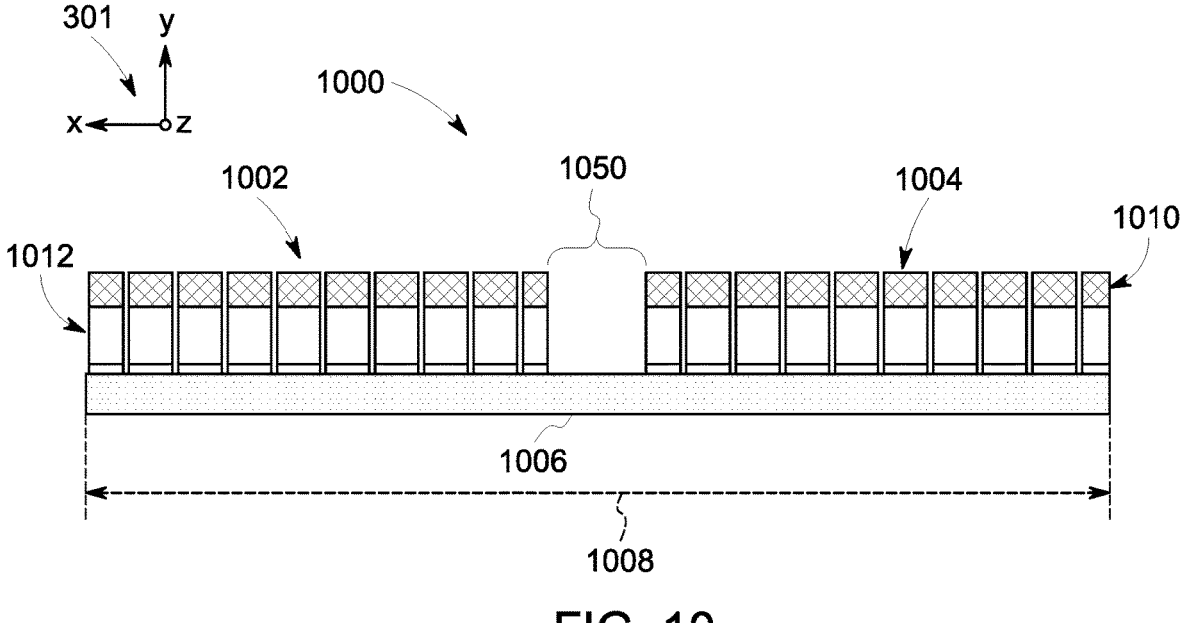
FIG. 10 shows another example of a transducer adapted with a shape memory material forming a backing layer of the transducer.
Figure 11:
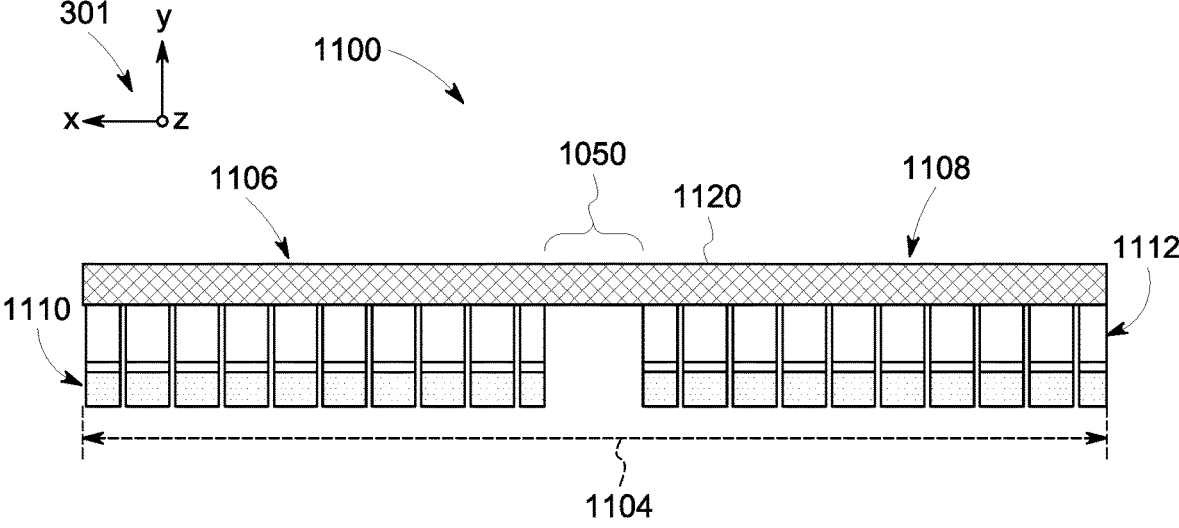
FIG. 11 shows another example of a transducer adapted with a shape memory material forming a matching layer of the transducer.

FIG. 10 shows a first example of a transducer 1000 with a SMP forming a backing layer. The transducer 1000 has a first transducer array 1002 and a second transducer array 1004, spaced away from one another along the x-axis separated by a space therebetween which is the location of the active region. A SMP 1006 extends between the transducer arrays and across an entire width 1008 of the transducer 1000, and may also span a length of the transducer and thus form a continuous backing layer across the area of the transducer 1000. Thus, each transducer array is coupled to a common backing layer and remaining components, e.g., a matching layer 1010 and an element 1012, of an acoustic stack of each transducer array may be laminated onto the SMP 1006. The transducer 1000 may be diced downwards, with respect to the y-axis, from a top of the matching layer 1010, through the element 1012 to a top of the SMP 1006. When forming the backing layer of the transducer 1000, the SMP 1006 may include an additive to lend the SMP 1006 attenuating properties. For example, the SMP 1006 may have an increased density and/or include silicone and tungsten as additives.

Alternatively, a SMP may form a matching layer of a transducer. A second example of a transducer 1100 is shown in FIG. 11 with a SMP 1102 forming a continuous matching layer extending entirely across a width 1104 of the transducer 1100. The transducer 1100 has a first transducer array 1106 and a second transducer array 1108. The transducer arrays are spaced apart from one another along the x-axis with the SMP 1102 extending between the transducer arrays. The transducer 1100 may be diced upwards, with respect to the y-axis, from a bottom of a backing layer 1110, through an element 1112, to a bottom of the SMP 1102. When forming the matching layer of the transducer 1100, the SMP 1102 may be formed of a base polymer.

By implementing a SMP as an acoustic layer of a transducer, rather than as a linkage between transducer arrays of the transducer, an adhering of the SMP to a backing layer (or matching layer) of the transducer arrays is precluded. Thus, fewer materials and components are demanded of a manufacturing process, thereby decreasing costs. Furthermore, shape-changing properties provided by the SMP are incorporated into the transducer without adding thickness to the transducers. A thickness, and a footprint of the transducer is maintained, e.g., not increased, while enhancing transducer gain.

Figure 12:
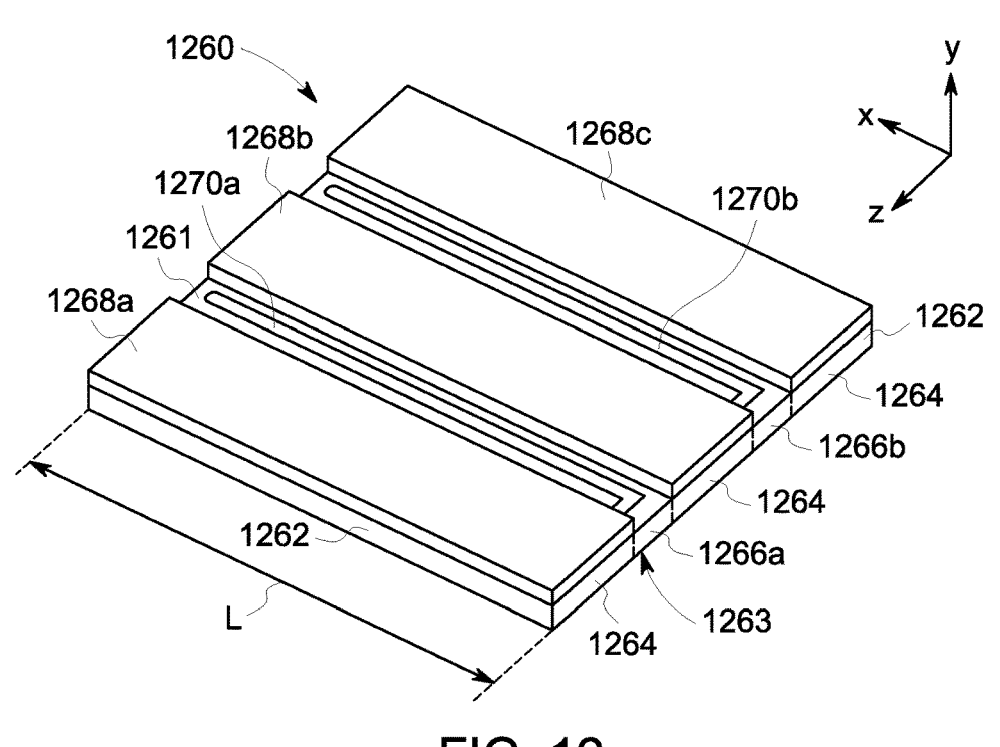
FIG. 12 shows one exemplary embodiment of a transducer comprising integral heating resistors configured to activate the shape memory material.

FIG. 12 depicts another embodiment where the SMP 1262 provides the backing layer for the entire area, or at least substantially the entire area, of the transducer 60. FIG. 12 shows only a portion of the transducer 1260. The transducer arrays are not shown in the figure so that the integrated circuits 1268a-1268c are visible. The integrated circuits may provide a mounting surface upon which the transducer arrays are mounted. Thus, the integrated circuits 1268a-1268c may be positioned between the SMP 1262 and the transducer arrays (not shown here).

Figure 13:
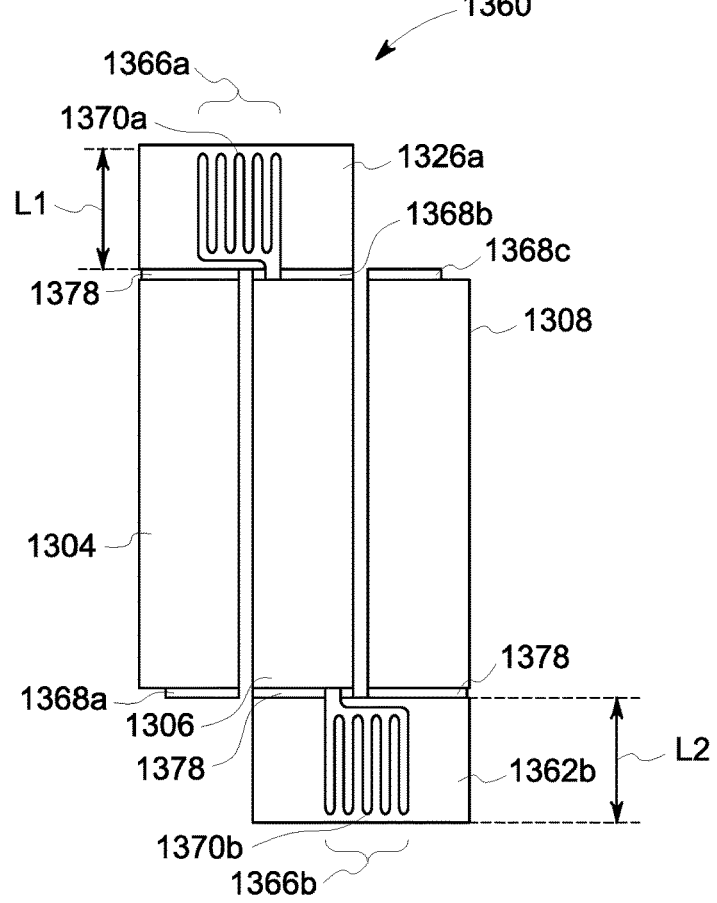
FIG. 13 shows another exemplary embodiment of a transducer comprising integral heating resistors configured to activate the shape memory material.

The integrated circuits 1268a-1268c may be, for example, application specific integrated circuits (ASICs) or may be general integrated circuits, such as microprocessors. Each ASIC 1268a-1268c is configured to receive and process signals from a respective transducer array. In the examples at FIGS. 12 and 13, there is a 1:1 ratio between integrated circuits and transducer arrays. FIG. 13 demonstrates the externally arranged SMP embodiment where the SMP is attached at the ends of the ASICs 1268a-1268c. Each of the three ASICs 1268a-1268c provides a backing surface and rigid substrate to which one of the transducer arrays 1304, 1306, 1308 is attached.

In other embodiments, one integrated circuit 1268 may be associated with a plurality of transducer arrays. For instance, an embodiment with three transducer arrays, such as those depicted above in FIGS. 7A-7C and 9A-9D, may have just one ASIC 1268 configured to receive and process acoustic signals from all three transducer arrays. In other embodiments, two ASICs may be provided for three transducer arrays, where the transducers signals are divided among the two ASICs. In still other embodiments, a greater number of ASICs than transducer arrays may be provided, where signals from one or more of the transducer arrays are divided among two or more ASICs.

In an embodiment where the SMP is thermally stimulated to change shape, an integral heating resistor 1270a, 1270b, 1370a, 1370b may be configured to provide a thermal stimulus to the SMP 1262 and cause the transducer 1260, 1360 to change configuration—e.g., transition from the folded configuration to the unfolded configuration, the rolled or curved configuration to the flat configuration, etc. The transducer 1260 may comprise a plurality of integral heating resistors, such as concentrated in the active region(s) 1266 thereof. The integral heating resistors 1270a, 1270b are configured to locally heat the immediate surrounding area of SMP, thus to provide a targeted stimulus.

In this way, a highly targeted and controllable thermal stimulus can be provided to specific portions of the SMP. Such local stimulation allows precise and controlled heat delivery. Since the integral heating resistor 1270, 1370 may be embedded in the SMP or adhered to a top surface of the SMP to provide targeted heat delivery to the active region, the applied heat will be maintained within the SMP and will not contact patient tissue or other electronics on the transducer 1260, 1360. This enables application of higher temperatures in a safe and controlled manner, which affords greater flexibility on SMP materials to be used and enables use of relatively high temperatures in a safe manner.

The transducer 1260 may comprise any number or configuration of integral heating resistors 1270, 1370 and FIGS. 12-14C show various configurations incorporating integral heating resistors 1270. In FIG. 12, one integral heating resistor 1270a, 1270b is located in each active region 1266, where the integral heating resistors 1270a, 1270b run normal to the bending direction and substantially the length L of the transducer along the x axis. In other embodiments, multiple integral heating resistors 1270 may be located in each active region 1266.

FIG. 13 depicts an arrangement of integral heating resistors 1370a, 1370b on an embodiment of a transducer 1360 with an external arrangement of SMP 1362. In this example, the external arrangement is a split arrangement where a first section of SMP 1362a connects between the first ASIC 1368a and the second ASIC 1368b, and a second section 1362b of the SMP connects between the second ASIC 1368b and the third ASIC 1368c. As described above, other external arrangements of SMP may be provided, such as where one continuous section of SMP connects between all of the plurality of ASICs 1368a-1368c. In this example, each ASIC 1368a-1368c connects to one or more of the SMP sections 1362a and/or 1362b at a connecting region 1378a. For example, the board of the ASIC may extend and connect to the respective SMP section 1362a, 1362b.

The integral heating resistors may be variously shaped and located to provide targeted stimulus for the thermal-activated SMP. FIG. 12 shows an example where the integral heating resistors 1270a, 1270b are each a loop running substantially the length L of the SMP. FIG. 13 shows an embodiment where the integral heating resistors 1370a, 1370b are serpentine-shaped. The serpentine integral heating resistors 1270a, 1370b in FIG. 13 run longitudinal parallel with the lengths L1, L2 of the SMP portions 1362a, 1362b. In other embodiments, the serpentine shape of the integral heating resistors 1370 may run perpendicular to the lengths L1, L2. In still other embodiments, the integral heating resistors may have a different shape or pattern, such as, but not limited to, a spiral, rectangular serpentine, honeycomb, planar, or a grid pattern. In certain examples, any such pattern may be embedded in the SMP or on a top and/or bottom surface thereof.

Referring again to FIG. 12, the SMP 1262 may comprise one or more active regions 1266 configured to change shape in order to adjust the configuration of the transducer 1260, such as between the folded shape and the planar shape as described above. The SMP 1262 may also include one or more planar regions 1264 that are configured to remain relatively flat in the various configurations, and thus to conform to the flat shape of the ASIC 1268 and/or the transducer array. The integral heating resistors 1270 are configured to conform the active region 1266 of the SMP 1262 moves the ASICs 1268a-1268c (and corresponding transducer arrays) between the one or more different configurations. In various embodiments, the integral heating resistors 1270 are configured to be flexible, and thus to bend and straighten as the active region 1266 grows and flattens, such as between the folded and unfolded configurations. Alternatively, or additionally, the integral heating resistors 1270 may be configured to conform as the active region 1266 contracts and expands or shrinks and stretches. As described above, the SMP 1262 may be configured to change between an expanded and contracted shape, such as in the example above shown and described with respect to FIG. 5B. In such embodiments, the integral heating resistors 1270 may be configured to adjust to such expansion and contraction, such as having a coiled or serpentine shape.

Passive integral resistors can be used as the integral heating resistors 1270, 1370. For example, thin film metals may be utilized, such as nichrome (NiCr), carbon, tantalum (Ta), nickel phosphorus (NiP), or other thin film metals appropriate for heat generation. The thin film metals may be deposited directly onto the SMP, such as by printing, evaporation, sputtering, or the like. In still other embodiments, the integral heating resistors 1270, 1370 may be deposited on the SMP by a low temperature deposition. In still other embodiments, the integral heating resistors 1270, 1370 may be formed by laminating or otherwise adhering a sheet containing the resistors to the SMP. Similarly, the integral heating resistors 1270, 1370 may be formed on a flex or a thin film that gets laminated to the SMP 1262. In further such examples, the ASIC 1268a-1268c may also be adhered to the flex or thin film that gets laminated to the top surface 1261, which may be, in some examples, a single sheet that is pre-formed and then adhered to the top surface 1261. Alternatively, the SMP could be cast onto a foil of the thin film metal material (or a foil adhered to the top or bottom surface of the SMP), and the thin film metal material could be then be patterned off of the surface of the SMP.

In certain embodiments, the integral heating resistors 1270, 1370, may be adhered to or formed on the top surface 1261 or the bottom surface 1263 of the SMP, or alternatively may be embedded into the SMP. For example, the SMP may be formed d in layers and the thin film metal applied between two or more successive layers.

Various SMP arrangements and materials may be utilized, which may have thermal-activated shape change properties or thermal-assisted shape change properties. For example, the SMP may be a one-way heat activated material, where the integral heating resistors 1270, 1370 are utilized and controlled to apply heat to activate transition between a first configuration and a second configuration. For instance, the one-way shape change material could be poly(ethylene glycol) (PEG) blends that are photo-curable and thermal activated. Alternatively, the SMP may be a two-way shape memory material so that the SMP may be adjust between two shapes in response to a stimulus. In such an embodiment, both stimuli may be thermal, or one may be thermal and the second stimulus may be a different stimulus. In embodiments where both stimuli are thermal, the first stimulus may be, for example, a first temperature and the second stimulus may be a second temperature, where the one or more integral heating resistors 1270, 1370 are controlled to apply each of the first and second temperatures. where the transition between the second configuration back to the first configuration is activated by a different means. For example, the second stimulus, could be ultraviolet applied to activate transition from the second configuration back to the first configuration. Alternatively or additionally, the transition may be mechanically assisted, where the stimulus is applied to change the properties of the SMP, such as to make the SMP more supple, and a mechanical element may be configured to assist in transitioning between one or both configurations, such as to assist in folding and/or unfolding the transducer arrays. For instance, the two-way shape change material could be n cross-linked linear poly (ε-caprolactone) (PCL), which is a linear commercially available polyester with a trade name CAPA 6800 (Perstorp UK Ltd., Warrington, UK).

Figure 14A:
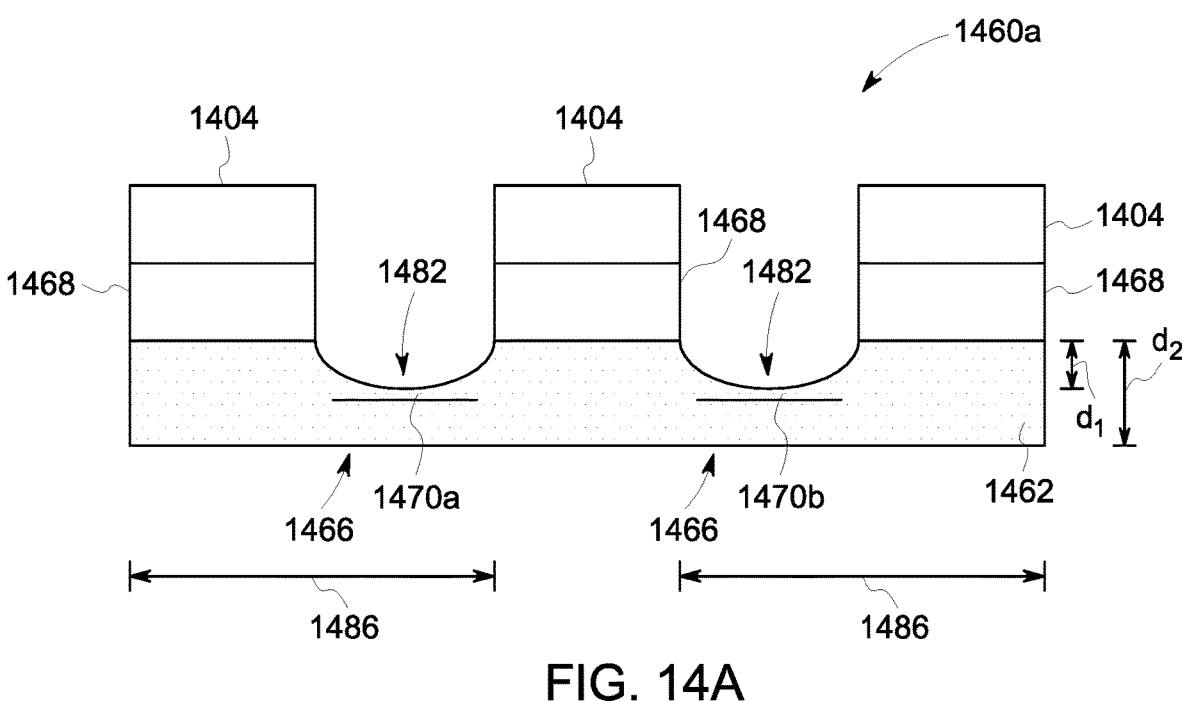
FIGS. 14A-14C show various embodiments of transducers having reliefs formed in the shape memory material and exemplary arrangements of integrated circuits and integral heating resistors with respect to the shape memory material and the reliefs.
Figure 14B:
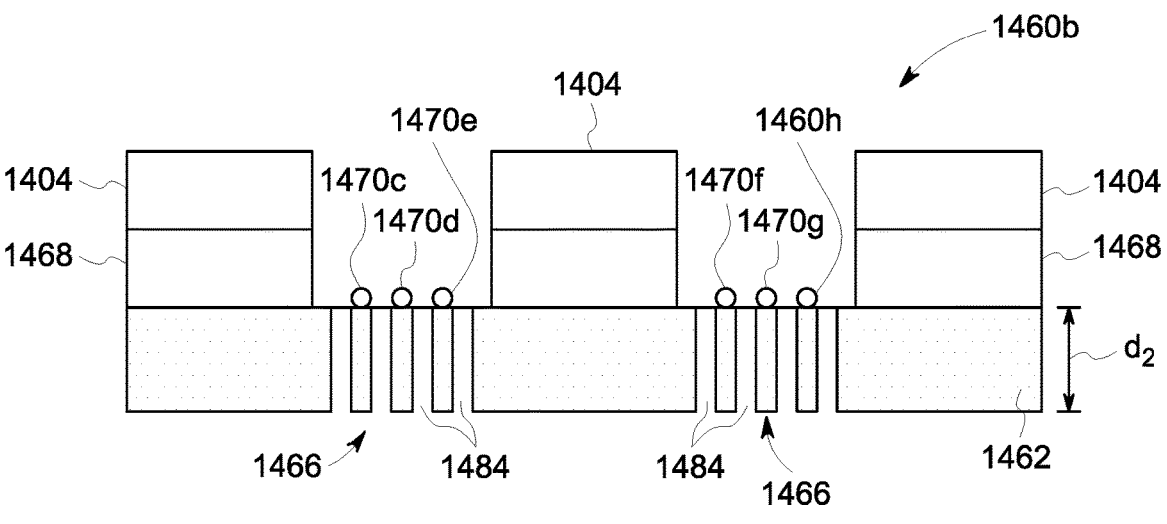
Figure 14C:
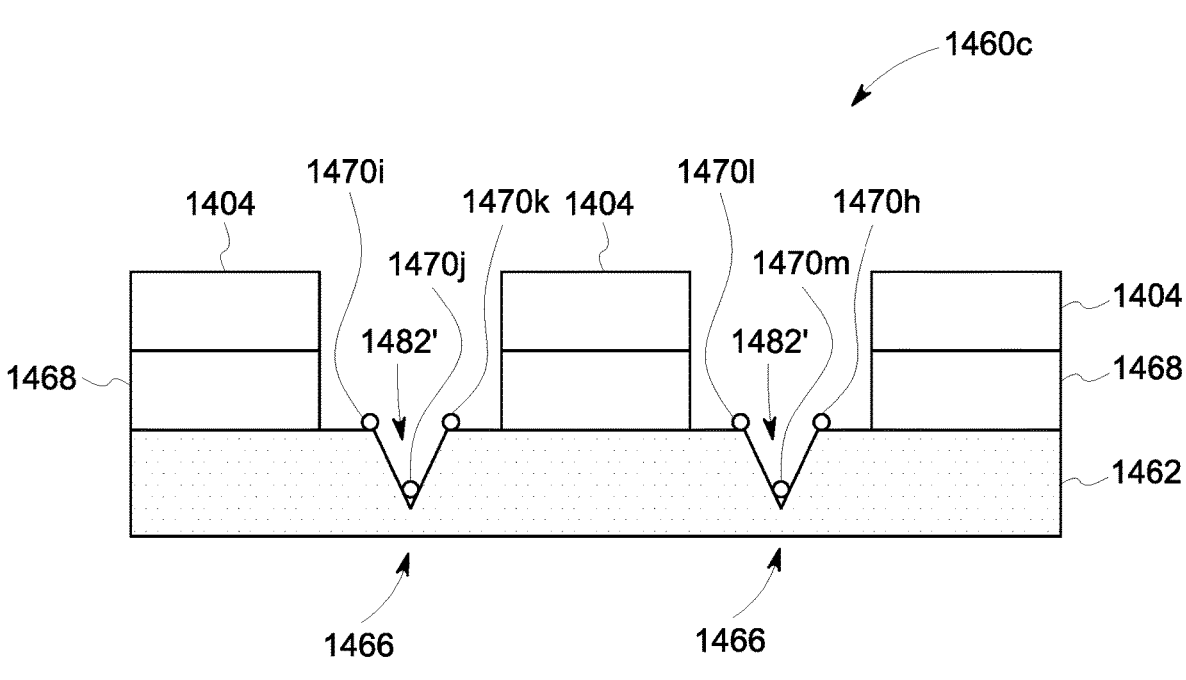

FIGS. 14A-14C depict embodiments of a transducer 1460a-1460c where each active region 1466 of the SMP 1462 includes one or more reliefs 1480 configured to facilitate movement by the SMP 1462, and particularly the active regions 1466, between the two or more shapes, or transducer configurations. For example, the reliefs 1480 may be formed by etching, limping, cutting, or otherwise creating a thinned region or portion within the active region 1466 of the SMP 1462. In these examples, the transducers 1460a-1460c each include three transducer arrays 1404 each having an associated ASIC 1468. In other embodiments, any number of two or more arrays may be utilized.

The ASICs 1468 are mounted to a top surface of the SMP 1462, where the SMP 1462 spans the full area of transducer 1460a-1460c and forms a backing layer for each of the plurality of ASICs 1468 and transducer arrays 1404. In other embodiments, the same relief 1480 structures could be applied in the external arrangements of the SMP described above. Likewise, the relief 1480 embodiments can be utilized with transducer 1460a-1460c arrangements depicted in FIGS. 14A-14D, such as where the ASICs 1468 are embedded into the SMP 1462 or where the ASICs 1468 form the backing layer and where the SMP only spans between the ASICs providing the active region 1466.

In FIG. 14A, the transducer 1460a includes a relief 1480 in each active region 1466 of the SMP 1462. The relief 1460 is a trough 1482 in the SMP, wherein the trough extends in a direction normal to the bending direction 1486 of the active region 1466. Thus, each trough 1482 extends longitudinally between the transducer arrays 1404. Each trough 1482 has a depth $d^1$ that is less than the depth $d^2$ of the SMP 1462. Thus, the trough 1482 is a recess in the active region 1466 that does not extend all the way through the SMP 1462, but only narrows, thins, or otherwise decreases the amount of SMP material in the active region 1466. This facilitates shape change of the active region 1466.

Various configurations of troughs 1482 may be provided and another trough configuration is exemplified at FIG. 14C. In certain embodiments, multiple troughs 1482 may run normal to the bending direction 1486 in the active region 1466, where multiple parallel and adjacent troughs run longitudinally between each adjacent pair of transducer arrays 1404. In other embodiments, the troughs or other relief formations may run in a different direction or may span only a portion of the length or width of the transducer area.

Integral heating resistors 1470 extend through the active regions 1466 to conduct signals to each of the ASICs 1468 as described above. The integral heating resistors 1470a-1470n may be variously configured with respect to the reliefs 1480. In FIG. 14A, the resistors 1470a, 1470b are embedded in the SMP 1462. For example, the embedded integral heating resistor 1470a, 1470b may be a serpentine-shaped wire or thin film deposit deposited on one layer of the SMP 1462 during manufacture. The integral heating resistor 1470a, 1470b is embedded below the trough 1482, below $d_1$, and configured to deliver heat in the region of the trough 1482. The combination of the heat delivery by the integral heating resistor 1470a, 1470b and the trough 1482 (or other relief formation) facilitate effective shape transition of the SMP 1462.

In other embodiments, such as that illustrated below with respect to FIGS. 14B-14C, the integral heating resistor 1470 may be deposited on or adhered to a top surface of the SMP 1462 in the region of the trough 1482 or may otherwise be configured to activate the active region 1466. For example, the integral heating resistor 1470 may be configured to accommodate shrinking or stretching of the SMP in the bending direction 1486. For example, the integral heating resistor 1470 may have a serpentine shape that winds normal to the bending direction 1486 and thus is configured to accommodate lateral movement—e.g., shrinking and stretching—of the active region 1466.

FIG. 14B illustrates an exemplary transducer 1460B wherein the relief 1480 comprises holes or slots 1484 in the SMP 1462 at the active region 1466. The holes or slots 1484 extend through the depth $d^2$ of the SMP 1462. For example, the holes or slots 1484 may form a grid-like pattern, or a meshing, that extends at least a portion of the longitudinal length between the transducer arrays 1404 and/or ASICs 1468. In other embodiments, the holes or slots 1484 may be formed at one or more locations along the longitudinal length of the active region 1466 to facilitate bending or shape change at that region.

The integral heating resistors 1470c-1470h are configured on SMP 1462 to extend over the holes or slots, such as where a flex or thin film is laminated to the top surface 1461 of the SMP 1462. Alternatively, the plurality of integral heating resistors 1470c-1470h may be printed on or otherwise applied to the SMP 1462 in such a way to avoid the plurality of holes or slots 1484. For example, the integral heating resistors 1470c-1470h may be printed or otherwise applied to top surface 1461 of the SMP 1462 in an area where the SMP is continuous across the active region 1466 between the ASICs 1468.

In various embodiments, the integral heating resistors 1470c-1470h may each be a separate device, such as a separately controlled conductive circuit, or may be electrically connected into one or more sets that are controlled as a unit to provide heating. For example, integral heating resistors 1470c-1470e may be connected as part of a first circuit, and integral heating resistors 1470f-1470h may be connected as part of a second circuit. Various other arrangements and combinations are possible.

FIG. 14C depicts another embodiment of a transducer 1460c wherein the SMP 1462 has trough-like reliefs 1480 running longitudinally and normal to the bending direction 1486 (see FIG. 14A). The troughs 1482' in FIG. 14C are triangular cutouts or divots in the active region 1466 configured to facilitate folding or other shape change. For example, the trough 1482 may be formed by etching, limping, cutting, or by other means for providing a thinned region or portion within the active region 1466 of the SMP 1462. The depth $d_1'$ of the trough 1482' is less than the depth $d_2$ of the SMP 1462. However, the depth $d_1'$ of the triangular trough 1482' is greater than the depth $d_1$ of the trough 1482 in FIG. 14A. However, both trough embodiments different proportional depth arrangements between $d_1$ and $d_2$ are possible and within the scope of the disclosure. In certain embodiments, it may be preferable for the depth $d_1$, $d_1'$ of the trough 1482, 1482' to be at least half or more of the depth $d_2$ of the SMP 1462.

In FIG. 14C, a plurality of integral resistors 1460i-1470k, 1470l-1470n are arranged on each trough 1482'. In the depicted example, one resistor runs longitudinally at the lowest point of the trough 1482' where the SMP is the thinnest. Additional resistors are arranged elsewhere in or around the trough 1482', and may be strategically placed to thermally activate the SMP as desired. In some embodiments the plurality of integral resistors 1460i-1470k, 1470l-1470n are each separately controllable to apply different heating amounts and/or apply thermal activation at different times in order to achieve a desired movement behavior of the SMP.

Figure 16A:
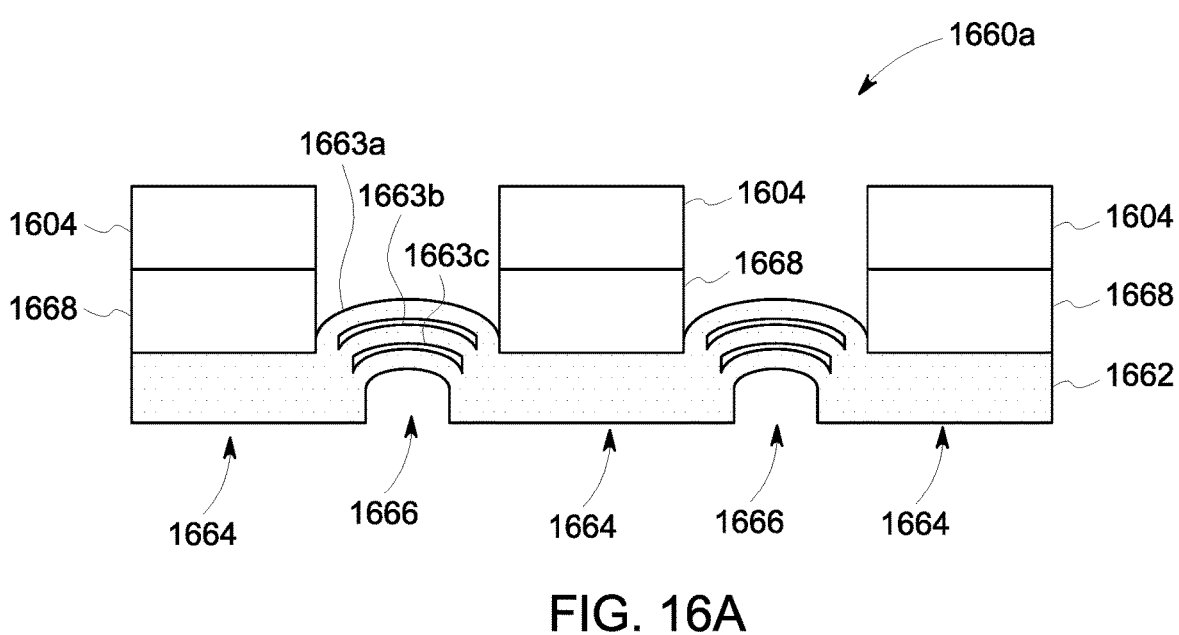
FIGS. 16A-16B show embodiments of transducers having layered active regions.
Figure 16B:
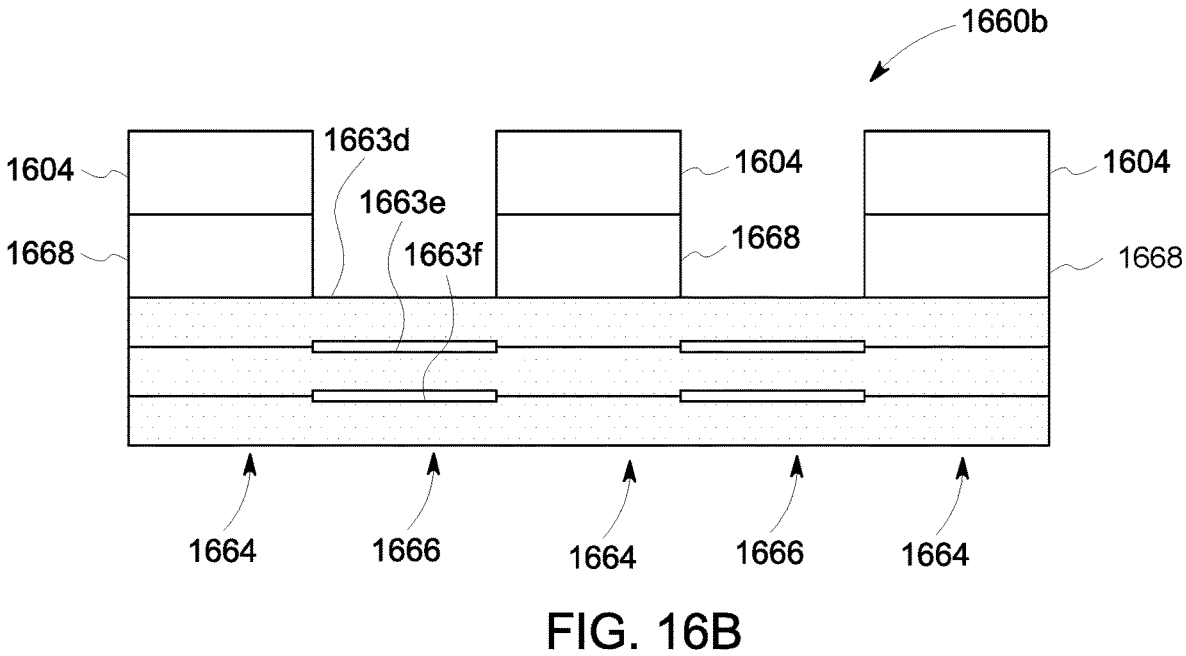

FIGS. 16A-16B depict embodiments of transducers 1660a and 1660b wherein the active region 1664 of the SMPs contain free-moving layers bound at the edges at or near the ASICs 1668 and transducer arrays 1604. The exemplary embodiments show three layers, but in other embodiments any number of two or more layers may be provided. The layers are configured to facilitate shape change, enabling increased movement of the arrays 1604 with respect to one another. The layers 1663 may have a curved shape when the transducer 1660a is in the unfolded configuration, as illustrated at FIG. 16a where the layers 1663a-1663c have a convex shape that curves upward. Alternatively, the layers 1663a-1663c could be arranged such that they have a concave shape that curves downward when the transducer 1660a is in the unfolded configuration. FIG. 16B shows another embodiment where the layers 1663d-1663f are flat when the transducer 1660a is in the unfolded configuration.

The planar regions 1664 may be one contiguous and homogeneous piece of SMP, as illustrated in FIG. 16A. Alternatively, the planar regions 1664 may be formed in layers that are bound together only at the planar regions 1664. Such an embodiment may enable application of integral heating resistors on one or more of the layers during manufacture so as to embed the integral heating resistors within the SMP.

Use of integral heating resistors enables fine control of the transition. Certain active regions 1266, 1366, 1466, 1666 or even portions of the active regions, may be stimulated one at a time and in an ordered succession. For example, a first active region 1266a, 1366a (FIGS. 12 and 13) may be stimulated first to change configuration of a first section of the transducer 1260, 1360, such as to move the first transducer array 1304 relative to the second array 1306 (e.g., to fold or unfold the SMP to transition between a stacked or unstacked configurations). The second region 1266b, 1366b may then follow. Additionally, the movement of the transducer portions can be precisely controlled by heating certain portions of the active region, such as certain layers of the SMP, in succession. In certain examples, the configuration change can be synchronized with beamforming.

The integral heating resistors 1270, 1370, 1470, 1670 may be connected to and powered by the ASICs 1268, 1368, 1468, 1668. In the embodiment at FIG. 13, for example, ASIC 1368b is connected to and controls the integral heating resistors 1370a and 1370b in each of the SMPs 1362a and 1362b. The ASICs 1268, 1368, 1468, 1668 may be configured to act as a control circuit for the integral heating resistors 1270, 1370, 1470, 1670, and thus to activate the resistors according to a predetermined routine to facilitate the transition between the first configuration and/or the second configuration. For example, the ASICs 1268, 1368, 1468, 1668 may be configured to control the timing of activation, the current delivered to each integral heating resistor 1270, 1370, 1470, 1670, and/or the temperature delivered to the SMP by the resistors.

In certain embodiments, the ASICs may communicate with the imaging system 20 (FIG. 1), such as to receive a command to transition the transducer between configurations. One or more of the ASICs 1268, 1368, 1468, 1668 may be then be configured to control the integral heating resistors 1270, 1370, 1470, 1670 accordingly to effectuate the commanded transition. In embodiments with multiple ASICs 1268, 1368, 1468, 1668, one or more of the ASICs may be configured to control the integral heating resistors 1270, 1370, 1470, 1670. Referring again to FIG. 12, the first ASIC 1268a is connected to and controls the first integral heating resistor 1270a. The second ASIC 1268b is connected to and controls the second integral heating resistor 1270b. Various other arrangements are possible, such as a single one of the ASICs controlling all of the integral heating resistors. Alternatively, one active region 1266, 1366, 1466, 1666 may include integral heating resistors 1270, 1370, 1470, 1670 controlled by multiple different ASICs.

Figure 15:
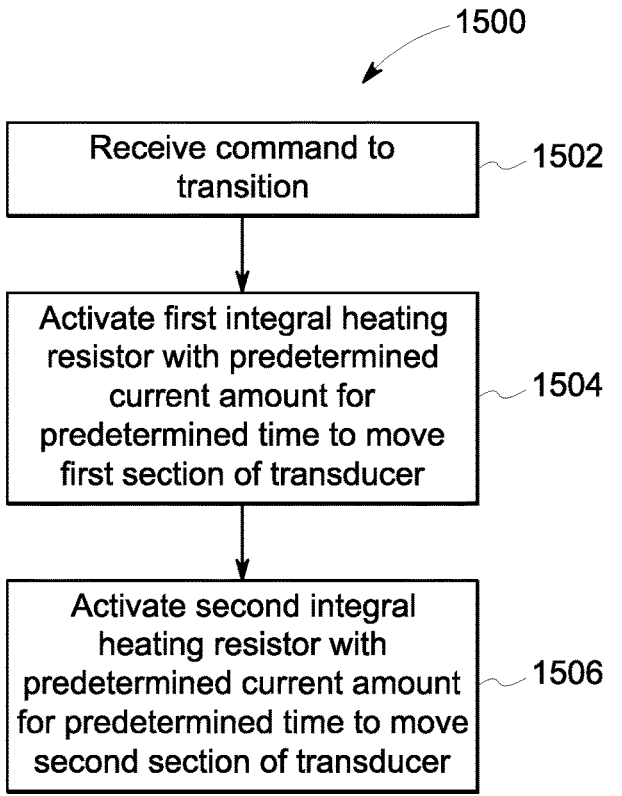
FIG. 15 depicts one embodiment of a method of deploying an imaging catheter.

FIG. 15 depicts one embodiment of a method 1500 of deploying an imaging catheter to transition between configurations. A command to transition is received at the control circuit at step 1502. For example, the control circuit may be one or more of the ASICs 1268, 1368, 1468, 1668, as described above. The command may be generated, for example, by the imaging system 20, and in particular a controller within the imaging system 20 configured to communicate commands to the control circuits within the catheter portion disposed inside the patient, such as the ASICs. Similarly, multiple ASICs (e.g. 1268a and 1268b) may be communicatively connected and configured to jointly control the one or more integral heating resistors. In response to receipt of the transition command, the one or more control circuits are configured to active integral heating resistors, such as according to a predetermined routine. In the example, a first integral heating resistor is controlled to heat the SMP and an active region by applying a predetermined current amount through the first integral heating resistor (e.g. 1270a) for a predetermined time. The SMP is thereby thermally activated to move a first end section of the transducer. Referencing the example of FIG. 12 to illustrate, the first integral heating resistor 1270a may be controlled to heat the first active region 1266a for a predetermined time and by applying a predetermined current so as to move a first portion of the transducer 1260, including the first ASIC 1268a and a first transducer array (not shown). For example, the first portion, or first subset of the transducer arrays) may be folded onto the middle portion such that the transducer arrays are stacked, as described in the examples above.

Next, a second integral heating resistor is activated by applying a predetermined current for a predetermined amount of time to move a second end section of the transducer containing a second subset of the transducer arrays. Referring again to the example at FIG. 12 for illustration, the second integral heating resistor 1270b may be activated with a predetermined current for a predetermined amount of time in order to heat the second active region 1266b and thereby move the second section of the transducer comprising the ASIC 1268c and associated transducer array(s). In various embodiments, the routine may be utilized to transition from the planer configuration shown in FIG. 12 to second configuration, or vice versa.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

We claim:

1. A deployable invasive device comprising:

a transducer with a plurality of elements linked by at least one shape memory material, the at least one shape memory material configured to move the plurality of elements relative to one another from a first configuration to a second configuration;

wherein the shape memory material comprises at least one active region configured to change shape to facilitate transition between the first configuration and the second configuration, wherein in the first configuration the plurality of elements are aligned in a plane, and wherein in the second configuration the plurality of elements are stacked; and at least one integral heating resistor on or within the at least one active region and configured to heat the shape memory material surrounding the integral heating resistor;

a control circuit configured to:

control the integral heating resistor to provide a first thermal stimulus to the at least one active region to move the plurality of elements in a first direction relative to one another from the first configuration to the second configuration; and control the integral heating resistor to provide a second thermal stimulus to the at least one active region to move the plurality of elements opposite the first direction relative to one another from the second configuration to the first configuration, wherein the second thermal stimulus is a different threshold temperature than the first thermal stimulus.

2. The device of claim 1, wherein the plurality of elements are arranged in a plurality of transducer arrays and the at least one shape memory material is configured to move the plurality of transducer arrays relative to one another.

3. The device of claim 1, further comprising the control circuit configured to receive a command to transition between the first configuration and the second configuration and to control current through the integral heating resistor in response to the command.

4. The device of claim 3, further comprising a plurality of integral heating resistors in each active region, wherein current through the plurality of integral heating resistors are separately controlled to execute the transition.

5. The device of claim 1, further comprising:

a first active region between a first subset of the plurality of elements and a second active region between a second subset of the plurality of elements; and at least a first integral heating resistor in the first active region and at least a second integral heating resistor in the second active region.

6. The device of claim 5, further comprising the control circuit configured to receive a command to transition between the first configuration and the second configuration and to control current through the first integral heating resistor to heat the first active region so as to move at least one of the first subset of the plurality of elements and to control current through the second integral heating resistor to heat the second active region so as to move at least one of the second subset of the plurality of elements.

7. The device of claim 1, wherein the shape memory material is configured to bend or shrink in response to the first thermal stimulus, and wherein the integral heating resistor is configured to bend as the shape memory material bends or shrinks.

8. The device of claim 1, further comprising at least one relief in the at least one active region configured to increase bendability of the active region of the shape memory material.

9. The device of claim 8, wherein the at least one relief comprises a trough in the shape memory material.

10. The device of claim 9, wherein the trough extends in a direction normal to a bending direction of the active region and wherein integral heating resistor is on or within the shape memory material at a location of the trough.

11. The device of claim 8, further comprising a plurality of reliefs, wherein the reliefs are holes or slots that extend through a depth of the shape memory material.

12. A method of deploying an imaging catheter, the method comprising:

receiving at a control circuit a command to transition a transducer from a first configuration to a second configuration, wherein in the first configuration the plurality of elements are aligned in a plane, and wherein in the second configuration the plurality of elements are stacked;

the transducer comprising a plurality of elements linked by at least one shape memory material, the at least one shape memory material configured to move the plurality of elements in a first direction relative to one another between the first configuration and the second configuration; and controlling current through at least one integral heating resistor to heat at least a portion of the shape memory material to provide the first thermal stimulus to move the plurality of elements relative to one another to transition the transducer from the first configuration to the second configuration; and receiving at the control circuit a command to transition the transducer from the second configuration to the first configuration; and providing, in response to control by the control circuit, a second thermal stimulus to move the plurality of elements opposite the first direction relative to one another to transition the transducer from the second configuration to the first configuration, wherein the second thermal stimulus is different temperature than the first thermal stimulus.

13. The method of claim 12, wherein the first thermal stimulus is provided by applying a first predetermined current magnitude through the integral heating resistor, and the second stimulus is a second thermal stimulus provided by applying a second predetermined current magnitude through the integral heating resistor.

14. The method of claim 12, wherein the transducer includes a first subset of the plurality of elements and a second subset of the plurality of elements, and further comprising controlling the current through at least a first integral heating resistor to heat a first active region so as to move at least one of the first subset of the plurality of elements and controlling current through at least a second integral heating resistor to heat a second active region so as to move at least one of the second subset of the plurality of elements.

15. The method of claim 12, wherein the transducer comprises a plurality of integral heating resistors on or within the shape memory material, wherein the method further includes separately controlling a magnitude and timing of current through the plurality of integral heating resistors to provide at least the first stimulus.

16. The method of claim 15, further comprising controlling at least a first one of the plurality of integral heating resistors to provide the first stimulus, and controlling at least a second one of the plurality of integral heating resistors to provide the second stimulus.

17. The method of claim 12, further comprising controlling current through the integral resistor to alternately provide each of the first stimulus and the second stimulus.

18. The device of claim 1, further comprising a plurality of integral heating resistors on or within the shape memory material, wherein the first thermal stimulus is a first temperature generated by at least one of the plurality of integral heating resistors, and the second stimulus is a second thermal stimulus being a second temperature generated by a different one of the plurality of integral heating resistors.

19. A deployable invasive device comprising:

a transducer with a plurality of elements linked by at least one shape memory material, the at least one shape memory material configured to move the plurality of elements relative to one another from a first configuration to a second configuration, wherein in the first configuration the plurality of elements are aligned in a plane, and wherein in the second configuration the plurality of elements are stacked;

wherein the shape memory material comprises at least one active region configured to change shape to facilitate transition between the first configuration and the second configuration; and at least one integral heating resistor on or within the at least one active region and configured to heat the shape memory material surrounding the integral heating resistor;

a control circuit configured to:

control the integral heating resistor to provide a first thermal stimulus to move the plurality of elements relative to one another from the first configuration to the second configuration; and control delivery of a second stimulus to move the plurality of elements relative to one another from the second configuration to the first configuration, wherein the second stimulus is different stimulus type than the first thermal stimulus.

20. The device of claim 19, wherein the second stimulus is ultraviolet.

* * * * *